(12) United States Patent
Alsina-Fernandez et al.

(10) Patent No.: US 9,764,004 B2
(45) Date of Patent: Sep. 19, 2017

(54) GLUCAGON RECEPTOR AGONISTS

(71) Applicant: Eli Lilly and Company, Indianapolis, IN (US)

(72) Inventors: Jorge Alsina-Fernandez, Indianapolis, IN (US); Tamer Coskun, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/293,324

(22) Filed: Oct. 14, 2016

(65) Prior Publication Data

US 2017/0112904 A1   Apr. 27, 2017

Related U.S. Application Data

(60) Provisional application No. 62/246,199, filed on Oct. 26, 2015.

(51) Int. Cl.
| | | |
|---|---|---|
| *A61K 38/26* | (2006.01) | |
| *A61P 3/10* | (2006.01) | |
| *A61P 7/12* | (2006.01) | |
| *C07K 14/605* | (2006.01) | |
| *C07K 14/00* | (2006.01) | |

(52) U.S. Cl.
CPC ............ *A61K 38/26* (2013.01); *C07K 14/001* (2013.01); *C07K 14/605* (2013.01)

(58) Field of Classification Search
None
See application file for complete search history.

(56) References Cited

U.S. PATENT DOCUMENTS

| | | | |
|---|---|---|---|
| 6,004,932 A | 12/1999 | Young et al. | |
| 7,452,966 B2 | 11/2008 | Glaesner et al. | |
| 8,450,270 B2 | 5/2013 | DiMarchi et al. | |
| 8,507,428 B2 | 8/2013 | DiMarchi et al. | |
| 8,546,327 B2 | 10/2013 | DiMarchi et al. | |
| 8,669,228 B2 | 3/2014 | DiMarchi et al. | |
| 8,703,701 B2 | 4/2014 | DiMarchi | |
| 8,900,593 B2 | 12/2014 | Day et al. | |
| 8,975,223 B2 | 3/2015 | Vignati et al. | |
| 9,040,660 B2 * | 5/2015 | Kofoed ................. | A61K 38/22 530/309 |
| 9,072,794 B2 | 7/2015 | Woo et al. | |
| 2011/0166062 A1 | 7/2011 | DiMarchi et al. | |
| 2012/0172295 A1 | 7/2012 | DiMarchi et al. | |
| 2012/0178670 A1 | 7/2012 | Riber et al. | |
| 2012/0329708 A1 | 12/2012 | DiMarchi et al. | |
| 2013/0059781 A1 * | 3/2013 | Kofoed ................. | A61K 38/22 514/12.3 |
| 2013/0116172 A1 | 5/2013 | DiMarchi et al. | |
| 2014/0011733 A1 | 1/2014 | Fosgerau et al. | |
| 2014/0011738 A1 | 1/2014 | DiMarchi | |
| 2014/0031278 A1 | 1/2014 | Lau et al. | |
| 2014/0100156 A1 | 4/2014 | Haack et al. | |
| 2014/0206607 A1 | 7/2014 | DiMarchi et al. | |
| 2014/0221281 A1 | 8/2014 | Haack et al. | |
| 2015/0051141 A9 | 2/2015 | Shandler et al. | |
| 2015/0111817 A1 | 4/2015 | Riber et al. | |
| 2015/0111826 A1 | 4/2015 | Riber et al. | |
| 2015/0182594 A1 | 7/2015 | Lau et al. | |
| 2015/0252091 A1 | 9/2015 | Bloom | |
| 2015/0274801 A1 | 10/2015 | Lau et al. | |
| 2015/0368311 A1 | 12/2015 | Haack et al. | |
| 2016/0199438 A1 | 7/2016 | Bokvist et al. | |
| 2016/0527729 | 9/2016 | Just et al. | |
| 2017/0008944 A1 | 1/2017 | Bossart et al. | |

FOREIGN PATENT DOCUMENTS

| | | | |
|---|---|---|---|
| WO | 2005000892 A2 | 1/2005 | |
| WO | 2009099763 A1 | 8/2009 | |
| WO | 2010070252 | 6/2010 | |
| WO | 2010071807 A1 | 6/2010 | |
| WO | 2011075393 A2 | 6/2011 | |
| WO | 2011087671 A1 | 7/2011 | |
| WO | 2011087672 A1 | 7/2011 | |
| WO | 2011119657 A1 | 9/2011 | |
| WO | WO2011131646 | * | 10/2011 |
| WO | 2013004983 A1 | 1/2013 | |
| WO | 2013164483 A1 | 11/2013 | |
| WO | 2013192130 A1 | 12/2013 | |
| WO | 2014170496 A1 | 10/2014 | |
| WO | 2015067715 A2 | 5/2015 | |
| WO | 2015067716 A1 | 5/2015 | |
| WO | 2015086731 | 6/2015 | |
| WO | 2015094875 A1 | 6/2015 | |
| WO | 2015094876 A1 | 6/2015 | |

(Continued)

OTHER PUBLICATIONS

Betts et al. Amino Acid Properties and Consequences of Substitutions. Chapter 14. Bioinformatics for Geneticists, 2003. pp. 289-316.*

Tan, T.M, et al., "Coadministration of Glucagon-Like Peptide-1 During Glucagon Infusion in Humans Results in Increased Energy Expenditure and Amelioration of Hyperglycemia," Diabetes, 62(4) Apr. 2013, pp. 1131-1138.

Finan, B., et al., "A Rationally Designed Monomeric Peptide Triagonist Corrects Obesity and Diabetes in Rodents," Nat. Med. Jan. 2015;21(1):27-36.

Cegla, J., et al., "Coinfusion of Low-Dose GLP-1 and Glucagon in Man Results in a Reduction in Food Intake," Diabetes, 2014; vol. 63, pp. 3711-3720.

(Continued)

*Primary Examiner* — Marcela M Cordero Garcia

(74) *Attorney, Agent, or Firm* — Matthew T. Lord

(57) ABSTRACT

The present invention relates to compounds with an extended duration of action at the glucagon receptor as compared to native glucagon. Specifically provided are glucagon receptor agonists with modifications to the structure of native glucagon introduced to selectively agonize the glucagon receptor over an extended period of time.

12 Claims, No Drawings

(56) References Cited

FOREIGN PATENT DOCUMENTS

| WO | 2015094878 A1 | 6/2015 |
| WO | 2015155141 | 10/2015 |
| WO | 2016043533 A1 | 3/2016 |
| WO | 2016108586 A1 | 7/2016 |
| WO | 2016108617 A1 | 7/2016 |
| WO | 2016166289 A1 | 10/2016 |
| WO | 2016198604 A1 | 12/2016 |
| WO | 2017003191 A1 | 1/2017 |

OTHER PUBLICATIONS

Bobe, G., et al., "Metabolic Responses of Lactating Dairy Cows to Single and Multiple Subcutaneous Injections of Glucagon," J. Dairy Sci., vol. 86, pp. 2072-2081, year 2003.

Nafikov, R.A., et al., "Prevention of Fatty Liver in Transition Dairy Cows by Subcutaneous Injections of Glucagon," J. Dairy Sci., vol. 89, pp. 1533-1545, year 2006.

* cited by examiner

GLUCAGON RECEPTOR AGONISTS

The present invention relates to compounds with an extended duration of action at the glucagon receptor as compared to native glucagon. Specifically provided are glucagon receptor agonists with modifications to the structure of native glucagon introduced to selectively agonize the glucagon receptor over an extended period of time. The glucagon receptor agonists may be useful either in combination with other therapeutic agents for treating disorders such as type 2 diabetes mellitus (T2DM) and/or obesity, or as monotherapies for treating a variety of disorders, such as obesity, non-alcoholic fatty liver disease (NAFLD), non-alcoholic steatohepatitis (NASH), dyslipidemia, metabolic syndrome, hyperinsulinemia and/or nighttime hypoglycemia, as well as fatty liver syndrome in dairy cows.

Over the past several decades, the prevalence of diabetes has continued to rise. T2DM is the most common form of diabetes accounting for approximately 90% of all diabetes. T2DM is characterized by high blood glucose levels caused by insulin resistance. The current standard of care for T2DM includes diet and exercise, and treatment with oral medications, and injectable glucose lowering drugs, including incretin-based therapies, such as glucagon-like-peptide-1 (GLP-1) receptor agonists and dipeptidyl peptidase IV (DPP-IV) inhibitors. When treatment with oral medications and incretin-based therapies are insufficient, treatment with insulin is considered. Patients whose disease has progressed to the point that insulin therapy is required are generally started on a single daily injection of a long-acting, basal insulin, although mealtime injections of rapid-acting insulins may be included, as necessary, in some cases.

Despite the availability of these therapies, blood glucose levels in many patients with T2DM still remain inadequately controlled. Uncontrolled diabetes leads to several conditions that impact morbidity and mortality of patients. One of the main risk factors for T2DM is obesity. The majority of T2DM patients (~90%) are overweight or obese. It is documented that a decrease in body adiposity will lead to improvement in obesity-associated co-morbidities including hyperglycemia and cardiovascular events. Therefore, therapies effective in glucose control and weight reduction are needed for better disease management.

In addition, the prevalence and awareness of nonalcoholic fatty liver disease (NAFLD)—which refers to a cluster of liver disorders associated with the accumulation of fat in the liver, and nonalcoholic steatohepatitis (NASH)—which is a severe form of NALFD characterized by histological findings such as inflammation, hepatocyte injury and fibrosis, have also continued to rise. NASH is the most common liver disease in western countries, and affects between 3-5% of adults in the United States. Treatment typically includes prescribed changes in diet and exercise, and may involve bariatric surgery, pioglitazones, statins, omega 3 and vitamin E therapy (in the case of non-diabetic NASH patients) to reduce liver fat, but there are no therapeutic agents approved to address the inflammation and/or fibrosis associated with NASH. Therefore additional therapies are needed.

Several peptides which are available and/or in development as therapeutic agents, including glucagon, are derived from pre-proglucagon, which is a polypeptide that is processed in tissue to form several structurally related peptides. Glucagon is a 29-amino acid peptide that corresponds with amino acids 53 to 81 of pre-proglucagon, having the following amino acid sequence: HSQGTFTSDYSKYLDSRRAQDFVQWLMNT (SEQ ID NO: 1). Glucagon helps maintain the level of glucose in the blood by binding to and activating glucagon receptors on hepatocytes, causing the liver to release glucose—stored in the form of glycogen—through a process called glycogenolysis. As glycogen stores become depleted, glucagon stimulates the liver to synthesize additional glucose by gluconeogenesis. This glucose is released into the bloodstream, preventing the development of hypoglycemia. Administration of glucagon is an established therapy for treating acute hypoglycemia, and emergency glucagon administration can restore normal glucose levels within minutes of administration. Certain glucagon analogs have been described as exhibiting improved solubility and stability. See, e.g., WO2015094875; WO2015094876; WO2015094878.

Other peptides derived from pre-proglucagon include GLP-1, glucagon-like-peptide-2 (GLP-2), and oxyntomodulin (OXM). GLP-1 is a 36 amino acid peptide, the major biologically active fragment of which (GLP-1$_{7-36}$) is produced as a 30-amino acid, C-terminal amidated peptide that corresponds with amino acids 98 to 127 of pre-proglucagon, having the following amino acid sequence: HAEGTFTSDVSSYLEGQAAKEFIAWLVKGR (SEQ ID NO: 2). Whereas glucagon stimulates the release of glucose to prevent hypoglycemia, GLP-1 (SEQ ID NO: 2) stimulates insulin synthesis and secretion and has been shown to prevent hyperglycemia in diabetics. A variety of GLP-1 analogs are currently available, including exenatide, liraglutide, albiglutide and dulaglutide.

OXM is a 37 amino acid peptide composed of the complete 29 amino acid sequence of glucagon with an octapeptide carboxy terminal extension (amino acids 82 to 89 of pre-proglucagon and termed "intervening peptide 1" or IP-1), having the following amino acid sequence: HSQGTFTSDYSKYLDSRRAQDFVQWLMNTKRNRNNIA (SEQ ID NO: 3). OXM activates both the glucagon and GLP-1 receptors, with a slightly higher potency for the glucagon receptor over the GLP-1 receptor. Analogs of OXM having dual glucagon receptor and GLP-1 receptor activity have been described. See, e.g., WO2011087672; WO2011087671.

Although not derived from pre-proglucagon, glucose-dependent insulinotropic polypeptide (GIP) is another peptide that plays a physiological role in glucose homeostasis by stimulating insulin secretion from pancreatic beta cells in the presence of glucose. GIP is a 42 amino acid peptide having the following amino acid sequence:

```
                                             (SEQ ID NO: 4)
  YAEGTFISDYSIAMDKIHQQDFVNWLLAQKGKKNDWKHNITQ.
```

Certain analogs of GIP have been described as exhibiting both GIP and GLP-1 receptor activity. See, e.g., WO2015067715; WO2011119657; WO2013164483.

In addition, similar to the dual activity of OXM described above, certain glucagon analogs have been described as having co-agonist activity both at the glucagon receptor and one or more of the GLP-1 or GIP receptors. For example, WO2011075393 and WO 2012177444, purport to describe glucagon analogs having activity at both the glucagon and GLP-1 receptors. Similarly, WO2013192130 purports to describe glucagon analogs also having activity at the GIP receptor. Further, WO2015067716 purports to describe analogs having triple agonist activity at each of the glucagon, GLP-1 and GIP receptors.

Despite the variety of peptides and proteins proposed as T2DM and/or obesity therapies, therapies that are currently available and/or in development have limitations. In particular, while the dual or triple agonists described above may be stated to provide the glucose-lowering properties of a GLP-1 receptor and/or GIP receptor agonist along with the metabolic benefits of a glucagon receptor agonist, the activity levels of such peptides at each of the various receptors they agonize are fixed, making it difficult to achieve an ideal receptor activation balance to obtain, in vivo, high efficacy with minimal side effects. And therapies which do not involve glucagon receptor agonism lack the potential metabolic benefits of such a mechanism of action.

While concomitant administration of glucagon may be theoretically capable of attenuating such limitations, currently available glucagon products are impractical for use in such applications. In particular, the plasma half-life of glucagon is less than an hour, making it impractical for chronic use, particularly in embodiments involving combinations with other therapies that are available and/or in development, as many such therapies are dosed as infrequently as once a day, and some are proposed for dosing as infrequently as once-weekly. In addition, wild type glucagon also has some activity at the GLP-1 receptor, which may complicate efforts to draw an appropriate balance of glucagon versus GLP-1 receptor activity in combination therapies wherein the other compound has its down GLP-1 receptor activity. Moreover, the solubility and chemical and physical stability characteristics of currently available glucagon products are also inappropriate for chronic use in such applications, and would not allow for co-formulation with other therapeutic agents.

Thus, there is a need for glucagon receptor agonists which have extended duration of action allowing for dosing as infrequently as once a day, thrice-weekly, twice-weekly or once a week. There is also a need for glucagon receptor agonists which have potent activity at the glucagon receptor, and high selectivity for activity at the glucagon receptor versus the GLP-1 receptor. There is also a need for glucagon receptor agonists with suitable characteristics to be co-formulated with other therapeutic agents. There is also a need for glucagon receptor agonists with solubility and stability characteristics allowing for long term storage and use.

The glucagon receptor agonists of the present invention seek to meet these needs. Accordingly, the present invention provides glucagon receptor agonists with an extended duration of action, allowing for dosing as infrequently as once a day, thrice-weekly, twice-weekly or once a week. The present invention provides glucagon receptor agonists with optimal and selective activity at the glucagon receptor as compared, for example, to the GLP-1 and/or GIP receptors. The present invention provides glucagon receptor agonists which have physical and chemical characteristics suitable for chronic use and co-formulation with other treatments. The present invention provides glucagon receptor agonists which, when used in combination with other diabetes treatments, result in enhanced glucose control, metabolic benefits, such as body weight lowering, and/or lipid benefits, such as PCSK9 lowering, when used in combination with other diabetes treatments. In particular, combinations of glucagon receptor agonists of the present invention with GLP-1R agonists or GIP-GLP-1 co-agonists have beneficial synergistic effects on measures such as weight loss and body composition. The present invention also seeks to provide effective treatments for other disorders when used as a monotherapy and/or in combination with other therapies, including obesity, NAFLD, NASH, dyslipidemia, metabolic disorder, hyperinsulinemia and/or nighttime hypoglycemia.

Accordingly, an embodiment of the present invention provides a glucagon receptor agonist comprising Formula I:

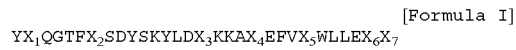

[Formula I]
YX$_1$QGTFX$_2$SDYSKYLDX$_3$KKAX$_4$EFVX$_5$WLLEX$_6$X$_7$ wherein
X$_1$ is Aib;
X$_2$ is T or L;
X$_3$ is Aib;
X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H, wherein a is 1 or 2 and b is 14 to 24;
X$_5$ is E or A;
X$_6$ is T or E;
X$_7$ is either absent, or is a peptide selected from the group consisting of GPSSGAPPPS and GPSSG;
and the C-terminal amino acid is optionally amidated (SEQ ID NO: 5);
or a pharmaceutically acceptable salt thereof.

Another embodiment of the present invention provides a glucagon receptor agonist comprising a formula consisting of Formula I:

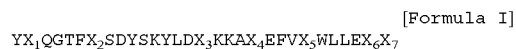

[Formula I]
YX$_1$QGTFX$_2$SDYSKYLDX$_3$KKAX$_4$EFVX$_5$WLLEX$_6$X$_7$ wherein
X$_1$ is Aib;
X$_2$ is T or L;
X$_3$ is Aib;
X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H, wherein a is 1 or 2 and b is 14 to 24;
X$_5$ is E or A;
X$_6$ is T or E;
X$_7$ is either absent, or is a peptide selected from the group consisting of GPSSGAPPPS and GPSSG;
and the C-terminal amino acid is optionally amidated (SEQ ID NO: 5);
or a pharmaceutically acceptable salt thereof.

Another embodiment of the present invention provides a glucagon receptor agonist consisting of Formula I:

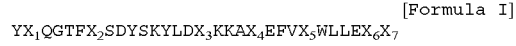

[Formula I]
YX$_1$QGTFX$_2$SDYSKYLDX$_3$KKAX$_4$EFVX$_5$WLLEX$_6$X$_7$ wherein
X$_1$ is Aib;
X$_2$ is T or L;
X$_3$ is Aib;
X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H, wherein a is 1 or 2 and b is 14 to 24;
X$_5$ is E or A;
X$_6$ is T or E;
X$_7$ is either absent, or is a peptide selected from the group consisting of GPSSGAPPPS and GPSSG;
and the C-terminal amino acid is optionally amidated (SEQ ID NO: 5);
or a pharmaceutically acceptable salt thereof.

In certain embodiments, the glucagon receptor agonist has the structure of Formula I wherein X$_2$ is T. In certain embodiments, the glucagon receptor agonist has the structure of Formula I wherein $X_2$ is L.

In certain embodiments, the glucagon receptor agonist has the structure of any of the above embodiments wherein $X_5$ is E. In certain embodiments, the glucagon receptor agonist has the structure of any of the above embodiments wherein $X_5$ is A.

In certain embodiments, the glucagon receptor agonist has the structure of any of the above embodiments wherein $X_6$ is T. In certain embodiments, the glucagon receptor agonist has the structure of any of the above embodiments wherein $X_6$ is E.

In certain embodiments, the glucagon receptor agonist has the structure of any of the above embodiments wherein $X_7$ is GPSSGAPPPS. In certain embodiments, the glucagon receptor agonist has the structure of any of the above embodiments wherein $X_7$ is GPSSG. In certain embodiments, the glucagon receptor agonist has the structure of any of the above embodiments wherein $X_7$ is absent.

In certain embodiments, the glucagon receptor agonist has the structure of any of the above embodiments wherein b is 16 to 20. In certain embodiments, the glucagon receptor agonist has the structure of any of the above embodiments wherein b is 16 to 18. In certain embodiments, the glucagon receptor agonist has the structure of any of the above embodiments wherein b is 16. In certain embodiments, the glucagon receptor agonist has the structure of any of the above embodiments wherein b is 18.

In certain embodiments, the glucagon receptor agonist has the structure of Formula I wherein: $X_2$ is T; a is 2; b is 16; $X_5$ is E; $X_6$ is T; and $X_7$ is GPSSGAPPPS; and wherein the C-terminal amino acid is amidated as a C-terminal primary amide (SEQ ID NO: 6).

In certain embodiments, the glucagon receptor agonist has the structure of Formula I wherein: $X_2$ is T; a is 2; b is 18; $X_5$ is E; $X_6$ is T; $X_7$ is GPSSGAPPPS; and wherein the C-terminal amino acid is amidated as a C-terminal primary amide (SEQ ID NO: 7).

In certain embodiments, the glucagon receptor agonist has the structure of Formula I wherein: $X_2$ is L; a is 2; b is 16; $X_5$ is E; $X_6$ is T; and $X_7$ is GPSSGAPPPS; and wherein the C-terminal amino acid is amidated as a C-terminal primary amide (SEQ ID NO: 8).

In certain embodiments, the glucagon receptor agonist has the structure of Formula I wherein: $X_2$ is T; a is 2; b is 16; $X_5$ is E; $X_6$ is T; and $X_7$ is GPSSG; and wherein the C-terminal amino acid is amidated as a C-terminal primary amide (SEQ ID NO: 9).

In certain embodiments, the glucagon receptor agonist has the structure of Formula I wherein: $X_2$ is T; a is 2; b is 18; $X_5$ is E; $X_6$ is T; and $X_7$ is GPSSG; and wherein the C-terminal amino acid is amidated as a C-terminal primary amide (SEQ ID NO: 10).

In certain embodiments, the glucagon receptor agonist has the structure of Formula I wherein: $X_2$ is T; a is 1; b is 16; $X_5$ is A; $X_6$ is E; and $X_7$ is absent (SEQ ID NO: 11).

In certain embodiments, the glucagon receptor agonist has the structure of Formula I wherein: $X_2$ is T; a is 1; b is 18; $X_5$ is A; $X_6$ is E; and $X_7$ is absent (SEQ ID NO: 12).

In certain embodiments, the glucagon receptor agonist has the structure of Formula I wherein: a is 2; $X_5$ is E; $X_6$ is T; $X_7$ is a peptide selected from the group consisting of GPSSGAPPPS and GPSSG; and the C-terminal amino acid is amidated (SEQ ID NO: 16).

In certain embodiments, the glucagon receptor agonist has the structure of Formula I wherein: $X_2$ is T; a is 1; $X_5$ is A; $X_6$ is E; and $X_7$ is absent (SEQ ID NO: 17).

In certain embodiments, the activity of the glucagon receptor agonist at the glucagon receptor is at least 100-fold higher than the activity of the glucagon receptor agonist at the GLP-1 receptor.

Another embodiment of the present invention provides a method of treating a disease selected from the group consisting of T2DM, obesity, fatty liver disease, NASH, dyslipidemia, metabolic syndrome, hyperinsulinemia and nighttime hypoglycemia, comprising administering to a patient in need thereof, an effective amount of a glucagon receptor agonist of the present invention.

Another embodiment of the present invention provides a method of treating fatty liver comprising administering to a bovine in need thereof, an effective amount of the glucagon receptor agonist of the present invention. In certain embodiments, the bovine is a dairy cow.

Another embodiment of the present invention provides a method of treating a disease selected from the group consisting of T2DM, obesity, fatty liver disease, NASH, dyslipidemia, metabolic syndrome, hyperinsulinemia and nighttime hypoglycemia, comprising administering to a patient in need thereof, an effective amount of a glucagon receptor agonist of the present invention in combination with an effective amount of one or more additional therapeutic agents. In certain embodiments the disease is T2DM. In certain embodiments the disease is obesity. In certain embodiments the disease is fatty liver disease. In certain embodiments the one or more additional therapeutic agents are selected from the group consisting of GLP-1R agonists, GIP-GLP-1 co-agonists, insulin receptor agonists, oxyntomodulins, metformin, thiazolidinediones, sulfonylureas, dipeptidyl peptidase-4 ("DPP-4") inhibitors, and sodium glucose co-transporter 2 ("SGLT2") inhibitors. In certain embodiments the additional therapeutic agent is a GLP-1R agonist. In certain embodiments the GLP-1R agonist is dulaglutide. In certain embodiments the additional therapeutic agent is a GIP-GLP-1 co-agonist. In certain embodiments the GIP-GLP-1 co-agonist has the structure of SEQ NO: 15. In certain embodiments the additional therapeutic agent is an insulin receptor agonist.

In certain embodiments, the glucagon receptor agonist has synergistic effects on weight loss and body composition when used in combination with an additional therapeutic agent, such as a GLP-1R agonist or a GIP-GLP-1 co-agonist.

Another embodiment of the present invention provides use of a glucagon receptor agonist of the present invention in therapy. Another embodiment of the present invention provides use of a glucagon receptor agonist of the present invention in treating a disease selected from the group consisting of T2DM, obesity, fatty liver disease, NASH, dyslipidemia, metabolic syndrome, hyperinsulinemia and nighttime hypoglycemia. In certain embodiments the disease is T2DM. In certain embodiments the disease is obesity. In certain embodiments the disease is fatty liver disease. In certain embodiments, the present invention provides a glucagon receptor agonist of the present invention for use in the treatment of fatty liver in a dairy cow.

Another embodiment of the present invention provides a glucagon receptor agonist of the present invention for use in simultaneous, separate, or sequential use in combination with one or more additional therapeutic agents for use in therapy. In certain embodiments the one or more additional therapeutic agents are selected from the group consisting of GLP-1R agonists, GIP-GLP-1 co-agonists, insulin receptor agonists, oxyntomodulins, metformin, thiazolidinediones, sulfonylureas, DPP-4 inhibitors, and sodium glucose co-transporter 2 ("SGLT2") inhibitors. In certain embodiments the additional therapeutic agent is a GLP-1R agonist. In certain embodiments the GLP-1R agonist is dulaglutide. In certain embodiments the additional therapeutic agent is a GIP-GLP-1 co-agonist. In certain embodiments the GIP-GLP-1 co-agonist has the structure of SEQ ID NO: 15.

Another embodiment of the present invention provides use of a glucagon receptor agonist of the present invention in the manufacture of a medicament for the treatment of T2DM, obesity, fatty liver disease, NASH, dyslipidemia, metabolic syndrome, hyperinsulinemia and nighttime hypoglycemia.

Another embodiment of the present invention provides a pharmaceutical composition comprising a glucagon receptor agonist of the present invention and a pharmaceutically acceptable carrier, diluent, or excipient. In certain embodiments, the pharmaceutical composition further comprises an additional therapeutic agent. In certain embodiments the additional therapeutic agent is selected from the group consisting of GLP-1R agonists, GIP-GLP-1 co-agonists, insulin receptor agonists, oxyntomodulins, metformin, thiazolidinediones, sulfonylureas, DPP-4 inhibitors, and SGLT2 inhibitors. In certain embodiments the additional therapeutic agent is a GLP-1R agonist. In certain embodiments the GLP-1R agonist is dulaglutide. In certain embodiments the additional therapeutic agent is a GIP-GLP-1 co-agonist. In certain embodiments the GIP-GLP-1 co-agonist has the structure of SEQ ID NO: 15. In certain embodiments the additional therapeutic agent is an insulin receptor agonist.

Another embodiment of the present invention provides a method of inducing non-therapeutic weight-loss comprising administration of an effective amount of a glucagon receptor agonist of the present invention.

Another embodiment of the present invention provides a method of treating fatty liver syndrome in a bovine, comprising administering to a bovine in need thereof, an effective amount of a glucagon receptor agonist of the present invention.

Another embodiment of the present invention provides a glucagon receptor agonist of the present invention for use in the treatment of fatty liver syndrome in a bovine.

When used herein the term "glucagon receptor agonists" means compounds comprising the amino acid sequence of native human glucagon (SEQ ID NO: 1), a glucagon analog, a glucagon derivative or a glucagon fusion protein, which bind to and activate the glucagon receptor, and maintain selective activity at the glucagon receptor relative to the GLP-1 receptor, resulting in an increase in serum glucose levels when administered as a monotherapy. Such binding characteristics and pharmacodynamic effects may be measured using known in vitro and in vivo methods, such as those described in the studies below. A glucagon analog is a molecule having a modification including one or more amino acid substitutions, deletions, inversions, or additions when compared with the amino acid sequence of native human glucagon (SEQ ID NO: 1). A glucagon derivative is a molecule having the amino acid sequence of native human glucagon (SEQ ID NO:1) or of a glucagon analog, but additionally having at least one chemical modification of one or more of its amino acid side groups, α-carbon atoms, terminal amino group, or terminal carboxylic acid group. A glucagon fusion protein is a heterologous protein comprising glucagon, a glucagon analog or a glucagon derivative and a second polypeptide, such as an immunoglobulin Fc region.

The activities of the glucagon receptor agonists of the present invention are also selective for the glucagon receptor relative to GLP-1 receptor. When used herein, the terms "selective . . . relative to," "selectivity" and "selective against" refer to a compound that displays 50-, 100-, 200-, 250-, 500- or 1000-fold higher potency for the glucagon receptor over the GLP-1 receptor. Such selectivity may be measured using known in vitro methods, such as those described in the studies below.

The glucagon receptor agonists of the present invention have extended time action profiles allowing for dosing as infrequently as once daily, thrice-weekly, twice-weekly or once-weekly. The time action profile of a glucagon receptor agonist may be measured using known pharmacokinetic test methods.

The extended time action profiles of the glucagon receptor agonists of the present invention are achieved through the use of a fatty acid moiety conjugated to the epsilon-amino group of the side chain of the lysine amino acid at position 20. The fatty acid is conjugated to the epsilon-amino group of a lysine side-chain through a linker, which comprises $[2-(2-Amino-ethoxy)-ethoxy]-acetyl)_2-(\gamma Glu)_a$, wherein a is 1 or 2. The fatty acid and the gamma-glutamic acid in the linker act as albumin binders, and provide the potential to generate long-acting compounds. The fatty acid conjugated to the epsilon-amino group of the side chain of the lysine amino acid at position 20 by way of the linker comprises —CO—$(CH_2)_b$—$CO_2H$ wherein b is 14 to 24. Thus, the complete linker-fatty acid structure comprises ($[2-(2-Amino-ethoxy)-ethoxy]-acetyl)_2-(\gamma Glu)_a$-CO—$(CH_2)_b$-$CO_2H$ wherein a is 1 or 2 and b is 14 to 24. As shown in the chemical structures of Examples 1-7 below, the first unit of [2-(2-Amino-ethoxy)-ethoxy]-acetyl is linked to the epsilon-amino group of the lysine side-chain. The second unit of [2-(2-Amino-ethoxy)-ethoxy]-acetyl is then attached to the amino-group of the first unit of [2-(2-Aminoethoxy)-ethoxy]-acetyl. Then, the first unit of γGlu is attached to the amino group of the second unit of [2-(2-Amino-ethoxy)-ethoxy]-acetyl through the γ-carboxyl group of the side-chain. When a=2, the second unit of γGlu is attached to the α-amino group of the first unit of γGlu through the γ-carboxyl group of the side-chain. Finally, the fatty acid is attached to the α-amino group of the first (when a=1) or second (when a=2) unit of γGlu.

The glucagon receptor agonists of the invention are preferably formulated as pharmaceutical compositions administered by parenteral routes (e.g., subcutaneous, intravenous, intraperitoneal, intramuscular, or transdermal). Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006). The, preferred route of administration is subcutaneous.

The glucagon receptor agonists of the present invention may react with any of a number of inorganic and organic acids to form pharmaceutically acceptable acid addition salts. Pharmaceutically acceptable salts and common methodology for preparing them are well known in the art. (See, e.g., P. Stahl, et al. Handbook of Pharmaceutical Salts: Properties, Selection and. Use, 2nd Revised Edition (Wiley-VCH, 2011)). Pharmaceutically acceptable salts of the present invention include trifluoroacetate, hydrochloride, and acetate salts.

One particular benefit provided by the selectivity of the glucagon receptor agonists of the present invention for the glucagon receptor over the GLP-1 receptor is the ability to provide flexible treatment options when glucagon receptor agonists of the present invention are administered in combination with additional therapeutic agents, such that the ratio of activity at the glucagon receptor to activity at the other receptor(s) (e.g., GLP-1, GIP and/or insulin receptor). Thus, in certain preferred embodiments, the present invention provides a method of treatment of T2DM in a patient comprising administering to a patient in need of such treatment an effective amount of a glucagon receptor agonist of the present invention, or a pharmaceutically acceptable salt thereof, in combination with an additional therapeutic agent. In certain embodiments, the additional therapeutic agent is selected from the group consisting of a GLP-1R agonist, a GIP-GLP-1 or an insulin receptor agonist.

When used herein, the term "additional therapeutic agent (s)," means other compound(s) known to have beneficial therapeutic effects, such as treatments for T2DM and/or obesity, which are currently available and/or in development, including for example GLP-1R agonists, GIP-GLP-1 co-agonists, insulin receptor agonists, oxyntoniodulins, metformin, thiazolidinediones, sulfonylureas, DPP-4 inhibitors, and SGLT2 inhibitors.

When used herein, the term "in combination with" means administration of the glucagon receptor agonist of the present invention either simultaneously, sequentially or in a single combined formulation with the one or more additional therapeutic agents.

When used herein, the term "GLP-1R agonist" refers to a compound comprising the amino acid sequence of native human GLP-1 (SEQ ID NO: 2), a GLP-1 analog, GLP-1 derivative or a GLP-1 fusion protein, which maintains activity at the GLP-1 receptor. GLP-1 receptor activity may be measured by methods known in the art, including using in vivo experiments and in vitro assays that measure GLP-1 receptor binding activity or receptor activation. A GLP-1 analog is a molecule having a modification including one or more amino acid substitutions, deletions, inversions, or additions when compared with the amino acid sequence of native human GLP-1 (SEQ ID NO: 2). A GLP-1 derivative is a molecule having the amino acid sequence of native human GLP-1 (SEQ ID NO:2) or of a GLP-1 analog, but additionally having at least one chemical modification of one or more of its amino acid side groups, a-carbon atoms, terminal amino group, or terminal carboxylic acid group. A GLP-1 fusion protein is a heterologous protein comprising GLP-1, a GLP-1 analog or a GLP-1 derivative and a second polypeptide, such as an immunoglobulin Fc region. GLP-1R agonists currently available and/or in development include exenatide, liraglutide, lixisenatide, albiglutide, dulaglutide and semaglutide. In certain preferred embodiments wherein a glucagon receptor agonist of the present invention is administered in combination with a GLP-1R agonist, the GLP-1R agonist is dulaglutide. See, e.g., U.S. Pat. No. 7,452,966.

When used herein, the term "GIP-GLP-1 co-agonist" refers to a compound which has activity at both the GIP and GLP-1 receptors. GIP receptor and GLP-1 receptor activity may be measured by methods known in the art, including using in vivo experiments and in vitro assays that measure GIP receptor and/or GLP-1 receptor binding activity or receptor activation. Although no GIP-GLP-1 co-agonists are currently available as T2DM treatments, multiple GIP analogs have been described as exhibiting both GIP and GLP-1 receptor activity, see, e.g., WO2013164483; WO 2011119657.

In certain preferred embodiments wherein a glucagon receptor agonist of the present invention__ is administered in combination with a GIP-GLP-1 co-agonist, the GIP-GLP-1 co-agonist has the following structure:

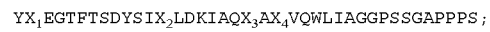

YX$_1$EGTFTSDYSIX$_2$LDKIAQX$_3$AX$_4$VQWLIAGGPSSGAPPPS;

wherein
X$_1$ is Aib;
X$_2$ is Aib;
X$_3$ is K which is chemically modified through conjugation to the epsilon-amino group of the K side-chain with ([2-(2-amino-ethoxy)-ethoxy]-acetyl)$_2$-(γGlu)$_a$-CO(CH$_2$)$_b$—CO$_2$H wherein a is 1 or 2 and b is 10 to 20;
X$_4$ is Phe or 1-naphthylalanine (1-Nal);
and the C-terminal amino acid is optionally amidated (SEQ ID NO: 13),
or a pharmaceutically acceptable salt thereof.

In certain preferred embodiments a is 2, b is 18; X$_4$ is 1-Nal; and the C-terminal amino acid is amidated as a C-terminal primary amide. (SEQ M NO: 14). In certain preferred embodiments a is 1, b is 18; X$_4$ is Phe; and the C-terminal amino acid is amidated as a C-terminal primary amide. (SEQ ID NO: 15). Such GIP-GLP-1 co-agonists may be prepared using techniques such as those which may be used to prepare glucagon receptor agonists of the present invention, as described below in the Peptide Synthesis examples.

When used herein, the term "insulin receptor agonist" refers to human insulin, or analogs or derivatives thereof, or any other protein which is capable of binding to and activating the insulin receptor. Insulin receptor activity may be measured by methods known in the art, including using in vivo experiments and in vitro assays that measure insulin receptor binding activity or receptor activation. An insulin analog is a molecule having a modification including one or more amino acid substitutions, deletions, inversions, or additions when compared with native human insulin, the structure of which is well known. An insulin derivative is a molecule having the amino acid sequence of native human insulin, or an analog thereof, but additionally having at least one chemical modification of one or more of its amino acid side groups, a-carbon atoms, terminal amino group, or terminal carboxylic acid group. An insulin fusion protein is a heterologous protein comprising insulin, an insulin analog or an insulin derivative portion and a second polypeptide. Although any insulin receptor agonist may be considered for use in embodiments wherein a glucagon receptor agonist of the present invention is administered in combination with an insulin receptor agonist, preferred insulin receptor agonists are those having a basal, or extended, duration of action. Currently available insulin receptor agonists with basal activity include insulin glargine, insulin determine, and insulin degludec, each of which is indicated for once-daily administration.

In certain embodiments, the present invention provides a method for treatment of T2DM in a patient comprising administering to a patient in need of such treatment an effective amount of a glucagon receptor agonist of the present invention, or a pharmaceutically acceptable salt thereof.

In certain embodiments, the present invention provides a method for treatment of obesity in a patient comprising administering to a patient in need of such treatment an effective amount of a glucagon receptor agonist of the present invention, or a pharmaceutically acceptable salt thereof.

In certain embodiments, the present invention provides a method for treatment of fatty liver disease in a patient comprising administering to a patient in need of such treatment an effective amount of a glucagon receptor agonist of the present invention, or a pharmaceutically acceptable salt thereof.

In certain embodiments, the present invention provides a method for treatment of NASH in a patient comprising administering to a patient in need of such treatment an effective amount of a glucagon receptor agonist of the present invention, or a pharmaceutically acceptable salt thereof.

In other embodiments, the present invention also provides a method of treatment of T2DM in a patient comprising administering to a patient in need of such treatment an effective amount of a glucagon receptor agonist of the present invention, or a pharmaceutically acceptable salt thereof, in combination with one or more additional therapeutic agents, such as GU-1R agonists, co-agonists, insulin receptor agonists, oxyntornodulins, metformin, thiazolidinediones, sulfonylureas, DPP-4 inhibitors, and SGLT2 inhibitors.

When used herein, the term "patient in need thereof" refers to a mammal, preferably a human or a bovine, with a disease or condition requiring treatment, including for example, T2DM, obesity, fatty liver disease, NASH and/or metabolic syndrome.

When used herein, the term "effective amount" refers to the amount or dose of glucagon receptor agonist of the present invention, or a pharmaceutically acceptable salt thereof which, upon single or multiple dose administration to the patient, provides the desired effect in the patient under diagnosis or treatment. An effective amount can be readily determined by a person of skill in the art through the use of known techniques and by observing results obtained under analogous circumstances. In determining the effective amount for a patient, a number of factors are considered, including, but not limited to: the species of mammal; its size, age, and general health; the specific disease or disorder involved; the degree of or involvement or the severity of the disease or disorder; the response of the individual patient; the particular glucagon receptor agonist administered; the mode of administration; the bioavailability characteristics of the preparation administered; the dose regimen selected; the use of concomitant medication; and other relevant circumstances.

Certain glucagon receptor agonists of the present invention are generally effective over a wide dosage range. For example, dosages for once-weekly administration may fall within the range of about 0.01 to about 30 mg per person per week. Glucagon receptor agonists of the present invention may be dosed daily, thrice-weekly, twice-weekly or once-weekly. Once-weekly administration is preferred.

As used herein, the term "treating" or "to treat" includes restraining, slowing, stopping, or reversing the progression or severity of an existing symptom or disorder.

The amino acid sequences of the present invention contain the standard single letter or three letter codes for the twenty naturally occurring amino acids. Additionally, "Aib" is alpha amino isobutyric acid. The present invention also encompasses novel intermediates and processes useful for the synthesis of glucagon receptor agonists of the present invention, or a pharmaceutically acceptable salt thereof. The intermediates and glucagon receptor agonists of the present invention may be prepared by a variety of procedures known in the art. In particular, the process using chemical synthesis is illustrated in the Examples below. The specific synthetic steps for each of the routes described may be combined in different ways to prepare glucagon receptor agonists of present invention. The reagents and starting materials are readily available to one of ordinary skill in the art.

The invention is further illustrated by the following examples, which are not to be construed as limiting.

PEPTIDE SYNTHESIS

EXAMPLE 1

Example 1 is a glucagon receptor agonist represented by the following description:

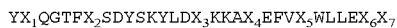

wherein $X_1$ is Aib; $X_2$ is T; $X_3$ is Aib; $X_4$ is K which is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H wherein a is 2 and b is 16; $X_5$ is E; $X_6$ is T; $X_7$ is GPSSGAPPPS; and the C-terminal amino acid is amidated as a C-terminal primary amide (SEQ ID NO: 6).

Below is a depiction of the structure of Example 1 using the standard single letter amino acid codes with the exception of residues Aib2, Aib16 and K20, where the structures of these amino acid residues have been expanded:

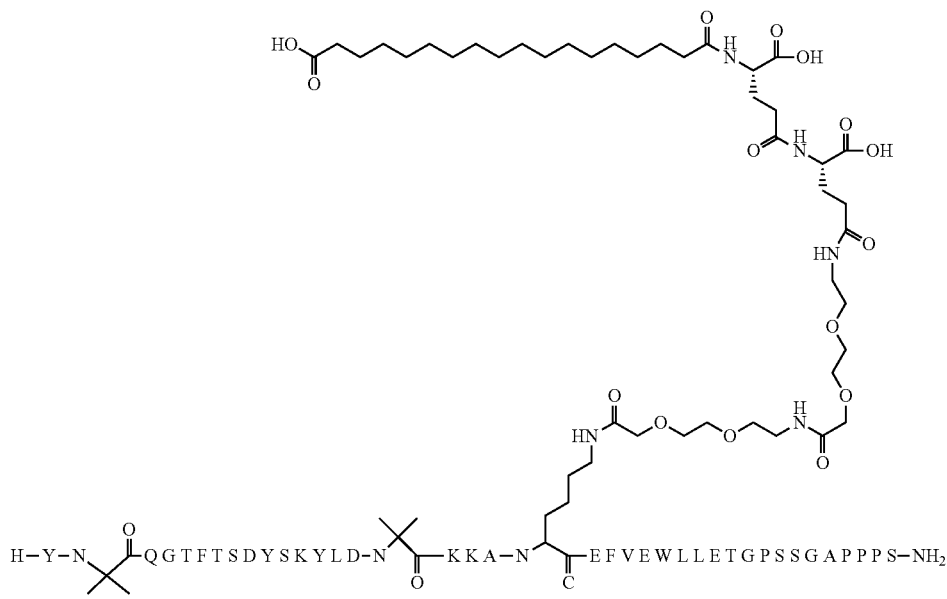

The peptide of Example 1 is generated by solid-phase peptide synthesis using a Fmoc/t-Bu strategy carried out on a Symphony automated peptide synthesizer (PTI Protein Technologies Inc.) starting from RAPP AM-Rink Amide resin and with couplings using 6 equivalents of amino acid activated with diisopropylcarbodiimide (DIC) and hydroxybenzotriazole (HOBt) (1:1:1 molar ratio) in dimethylformamide (DMF) for 90 min at 25° C.

Extended couplings for Pro31 (4 h), Trp25 (4 h), Glu24 (4 h), Val23 (10 h), Glu21 (4 h), Aib16 (4 h), Asp15 (4 h), Thr7 (4 h), Thr5 (4 h), Gly4 (4 h), Gln3 (4 h) and Aib2 (24 h) are necessary to improve the quality of the crude peptide. A Fmoc-Lys(Alloc)-OH building block is used for Lys20 coupling (orthogonal protecting group) to allow for site specific attachment of the fatty acid moiety later on in the synthetic process. The N-terminal residue is incorporated as Boc-Tyr (tBu)-OH using DIC-HOBt protocols as described above (24 h coupling).

After finishing the elongation of the peptide-resin described above, the Alloc protecting group present in Lys20 is removed using catalytic amounts of $Pd(PPh_3)_4$ in the presence of $PhSiH_3$ as a scavenger. Additional coupling/deprotection cycles using a Fmoc/t-Bu strategy to extend the Lys20 side-chain involve $Fmoc-NH-PEG_2-CH_2COOH$ (ChemPep Catalog #280102), Fmoc-Glu(OH)-OtBu (ChemPep Catalog #100703) and $HOOC-(CH_2)_{16}-COOtBu$. In all couplings, 3 equivalents of the building block are used with PyBOP (3 equiv) and DIEA (6 equiv) in DMF for 4h at 25° C.

Concomitant cleavage from the resin and side chain protecting group removal are carried out in a solution containing trifluoroacetic acid (TFA):triisopropylsilane:1, 2-ethanedithiol:water:thioanisole 90:4:2:2:2 (v/v) for 2 h at 25° C. followed by precipitation with cold ether. Crude peptide is purified to >99% purity (15-20% purified yield) by reversed-phase HPLC chromatography with water/acetonitrile (containing 0.05% v/v TFA) gradient on a C18 column, where suitable fractions are pooled and lyophilized, resulting in a TFA salt.

In a synthesis performed essentially as described above, the purity of Example 1 is examined by analytical reversed-phase HPLC, and identity is confirmed using LC/MS (observed: $M+3H^+/3=1713.6$; Calculated $M+3H^+/3=1714.3$; observed: $M+4H^+/4=1285.7$; Calculated $M+4H^+/4=1285.9$).

EXAMPLE 2

Example 2 is a glucagon receptor agonist represented by the following description:

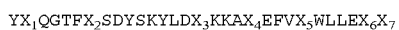

$YX_1QGTFX_2SDYSKYLDX_3KKAX_4EFVX_5WLLEX_6X_7$ wherein: $X_1$ is Aib, $X_2$ is T; $X_3$ is Aib; $X_4$ is K which is chemically modified through conjugation to the epsilon-amino group of the K side-chain with ([2-(2-Amino-ethoxy)-ethoxy]-acetyl)$_2$-($\gamma$Glu)$_a$-CO-(CH$_2$)$_b$-CO$_2$H; a is 2; b is 18; $X_5$ is E; $X_6$ is T; $X_7$ is GPSSGAPPPS; and wherein the C-terminal amino acid is amidated as a C-terminal primary amide (SEQ ID NO: 7).

Below is a depiction of the structure of Example 2 using the standard single letter amino acid codes with the exception of residues Aib2, Aib16 and K20, where the structures of these amino acid residues have been expanded:

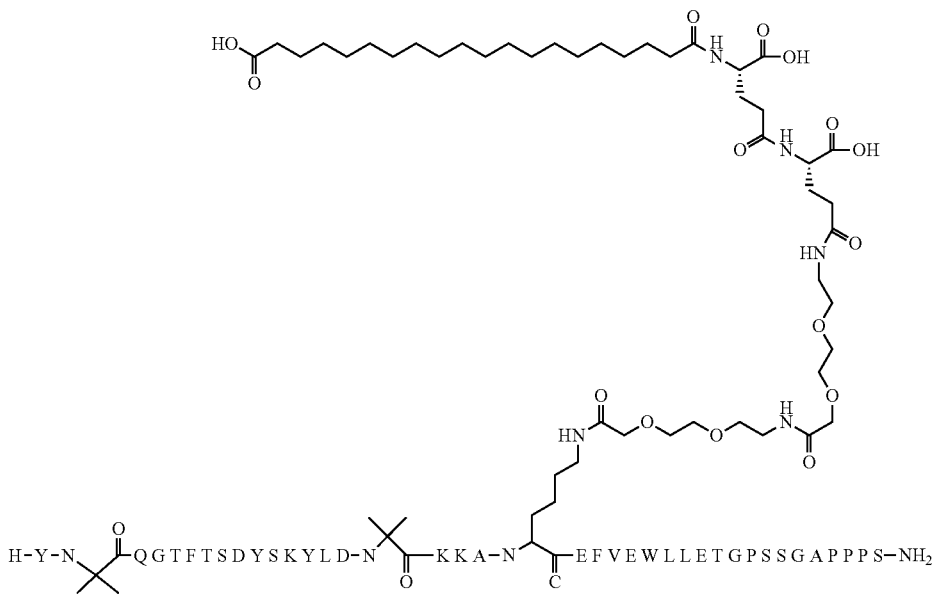

The peptide according to Example 2 is synthesized similarly as described above in Example 1. HOOC—$(CH_2)_{18}$—COOtBu is incorporated using 3 equivalents of the building block with PyBOP (3 equiv) and DIEA (6 equiv) in DMF for 4 h at 25° C.

In a synthesis performed essentially as described above for Example 1, the purity of Example 2 is examined by analytical reversed-phase HPLC, and identity is confirmed using LC/MS (observed: M+3H$^+$/3=1723.2; Calculated M+3H$^+$/3=1723.6; observed: M+4H$^+$/4=1292.9; Calculated M+4H$^+$/4=1293.0).

EXAMPLE 3

Example 3 is a glucagon receptor represented by the following description:

$YX_1QGTFX_2SDYSKYLDX_3KKAX_4EFVX_5WLLEX_6X_7$ wherein: $X_1$ is Aib; $X_2$ is L; $X_3$ is Aib; $X_4$ is K which is chemically modified through conjugation to the epsilon-amino group of the K side-chain with ([2-(2-Amino-ethoxy)-ethoxy]-acetyl)$_2$-($\gamma$Glu)$_a$-CO—$(CH_2)_b$—$CO_2H$; a is 2; b is 16; $X_5$ is E; $X_6$ is T; and $X_7$ is GPSSGAPPPS; and wherein the C-terminal amino acid is amidated as a C terminal primary amide (SEQ ID NO: 8).

Below is a depiction of the structure of Example 3 using the standard single letter amino acid codes with the exception of residues Aib2, Aib16 and K20, where the structures of these amino acid residues have been expanded:

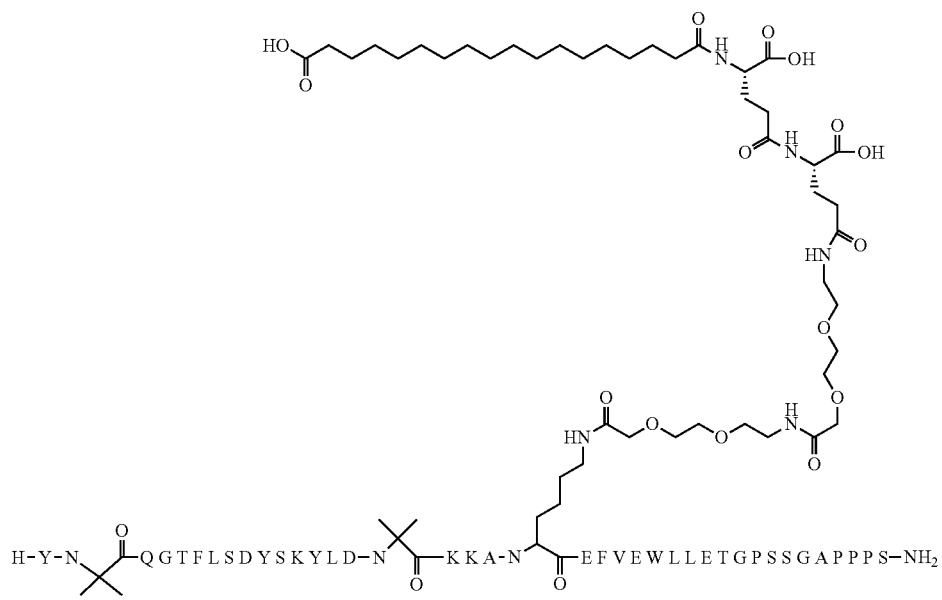

The peptide according to Example 3 is synthesized similarly as described above for Example 1.

In a synthesis performed essentially as described above for Example 1, the purity of Example 3 is examined by analytical reversed-phase HPLC, and identity is confirmed using LC/MS (observed: $M+3H^+/3=1717.4$; Calculated $M+3H^+/3=1718.3$; observed: $M+4H^+/4=1288.3$; Calculated $M+4H^+/4=1289.0$).

EXAMPLE 4

Example 4 is a glucagon receptor agonist represented by the following description:

$YX_1QGTFX_2SDYSKYLDX_3KKAX_4EFVX_5WLLEX_6X_7$ wherein $X_1$ is Aib; $X_2$ is T; $X_3$ is Aib; $X_4$ is K which is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H; a is 2; b is 16; $X_5$ is E; $X_6$ is T; and $X_7$ is GPSSG; and the C-terminal amino acid is amidated as a C-terminal primary amide (SEQ ID NO: 9).

Below is a depiction of the structure of Example 4 using the standard single letter amino acid codes with the exception of residues Aib2, Aib16 and K20, where the structures of these amino acid residues have been expanded:

The peptide according to Example 4 is synthesized similarly as described above for Example 1.

In a synthesis performed essentially as described above for Example 1, the purity of Example 4 is examined by analytical reversed-phase HPLC, and identity is confirmed using LC/MS (observed: $M+3H^+/3=1563.7$; Calculated $M+3H^+/3=1564.4$; observed: $M+4H^+/4=1172.9$; Calculated $M+4H^+/4=1173.6$).

EXAMPLE 5

Example 5 is a glucagon receptor agonist represented by the following description:

$YX_1QGTFX_2SDYSKYLDX_3KKAX_4EFVX_5WLLEX_6X_7$ wherein $X_1$ is Aib; $X_2$ is T; $X_3$ is Aib; $X_4$ is K which is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H; a is 2; b is 18; $X_5$ is E; $X_6$ is T; and $X_7$ is GPSSG; and the C-terminal amino acid is amidated as a C-terminal primary amide (SEQ ID NO: 10).

Below is a depiction of the structure of Example 5 using the standard single letter amino acid codes with the exception of residues Aib2, Aib16 and K20, where the structures of these amino acid residues have been expanded:

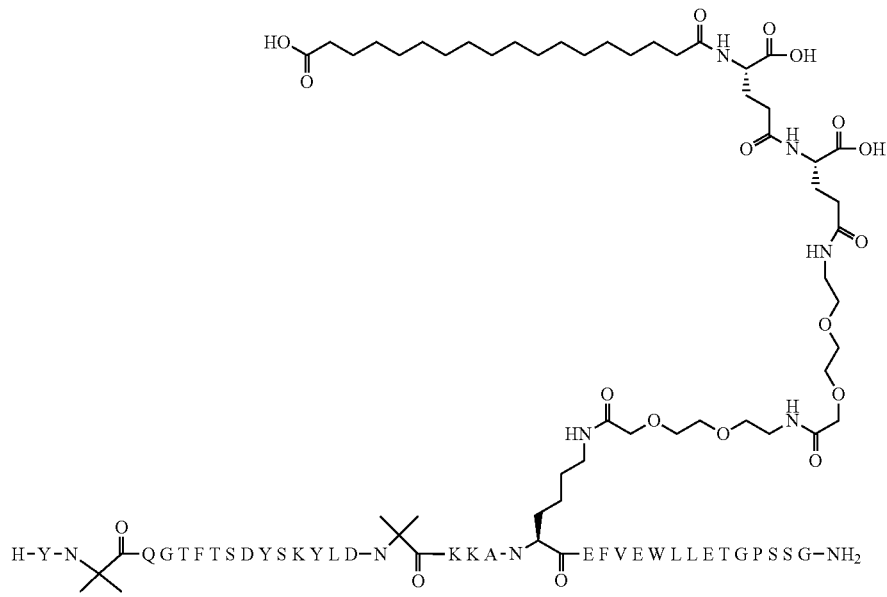

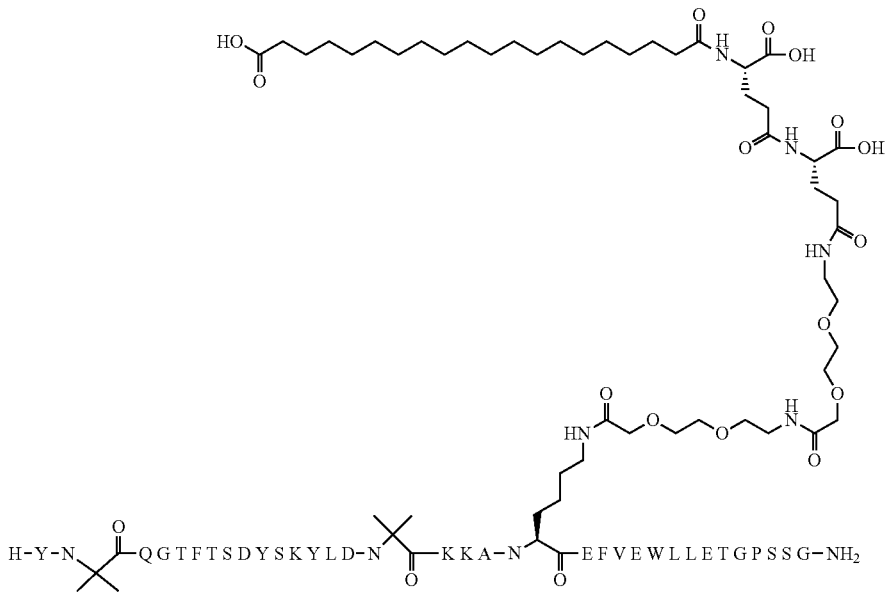

The peptide according to Example 5 is synthesized similarly as described above for Example 1.

In a synthesis performed essentially as described above for Examples 1 and 2, the purity of Example 5 is examined by analytical reversed-phase HPLC, and identity is confirmed using LC/MS (observed: M+3H$^+$/3=1572.9; Calculated M+3H$^+$/3=1573.8; observed: M+4H$^+$/4=1179.8; Calculated M+4H$^+$/4=1180.6).

EXAMPLE 6

Example 6 is a glucagon receptor represented by the following description:

YX$_1$QGTFX$_2$SDYSKYLDX$_3$KKAX$_4$EFVX$_5$WLLEX$_6$X$_7$ wherein X$_1$ is Aib; X$_2$ is T; X$_3$ is Aib; X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H; a is 1; b is 16; X$_5$ is A; X$_6$ is E; and X$_7$ is absent; and the C-terminal amino acid is C-terminal acid (SEQ ID NO: 11).

Below is a depiction of the structure of Example 6 using the standard single letter amino acid codes with the exception of residues Aib2, Aib16 and K20, where the structures of these amino acid residues have been expanded:

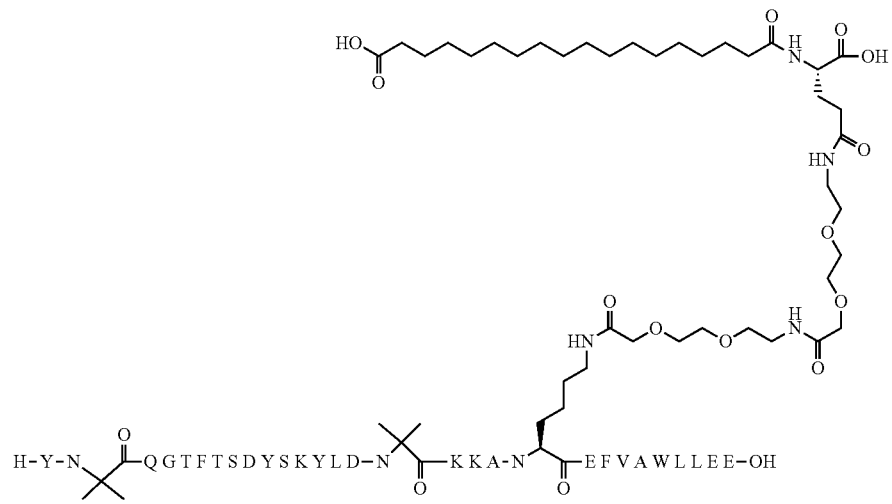

The peptide according to Example 6 is generated by solid-phase peptide synthesis using a Fmoc/t-Bu strategy carried out on a Symphony automated peptide synthesizer (PTI Protein Technologies Inc.) starting from Fmoc-L-Glu (OtBu)-Wang resin (NovaBiochem catalog item #856008; initial loading 0.51 mmol/g) and with couplings using 6 equivalents of amino acid activated with diisopropylcarbodiimide (DIC) and hydroxybenzotriazole (HOBt) (1:1:1 molar ratio) in dimethylformamide (DMF) for 90 min at 25° C.

Extended couplings for Trp25 (4 h), Ala24 (4 h), Val23 (10 h), Glu21 (4 h), Aib16 (4 h), Asp15 (4 h), Thr7 (4 h), Thr5 (4 h), Gln3 (4 h) and Aib2 (24 h) are necessary to improve the quality of the crude peptide. A Fmoc-Lys (Alloc)-OH building block is used for Lys20 coupling (orthogonal protecting group) to allow for site specific attachment of the fatty acid moiety later on in the synthetic process (4 h coupling time). The N-terminal residue is incorporated as Boc-Tyr(tBu)-OH using DIC-HOBt protocols as described above (24 h coupling).

served: $M+3H^+/3=1382.7$; Calculated $M+3H^+/3=1383.3$; observed: $M+4H^+/4=1036.6$; Calculated $M+4H^+/4=1037.7$).

EXAMPLE 7

Example 7 is a glucagon receptor agonist represented by the following description:

YX$_1$QGTFX$_2$SDYSKYLDX$_3$KKAX$_4$EFVX$_5$WLLEX$_6$X$_7$ wherein $X_1$ is Aib; $X_2$ is T; $X_3$ is Aib; $X_4$ is K which is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H; a is 1; b is 18; $X_5$ is A; $X_6$ is E; and $X_7$ is absent; and the C-terminal amino acid is C-terminal acid (SEQ ID NO: 12).

Below is a depiction of the structure of Example 7 using the standard single letter amino acid codes with the exception of residues Aib2, Aib16 and K20, where the structures of these amino acid residues have been expanded:

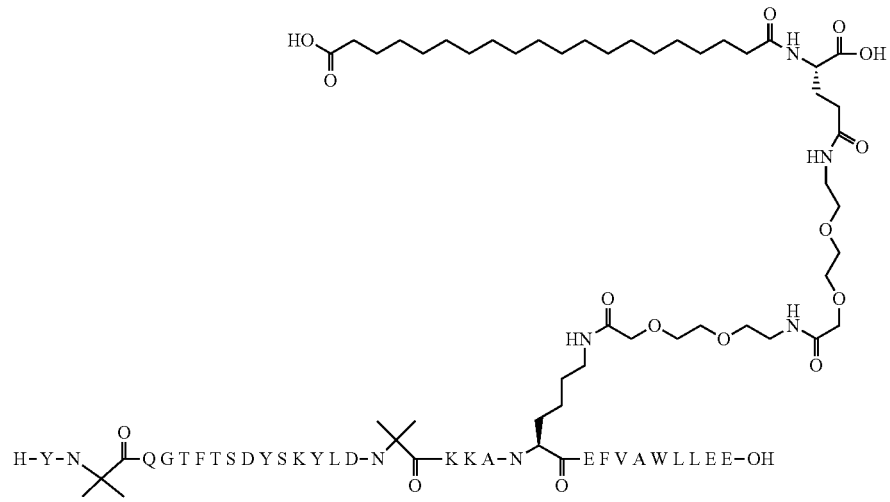

After finishing the elongation of the peptide-resin described above, the Alloc protecting group present in Lys20 is removed using catalytic amounts of Pd(PPh$_3$)$_4$ in the presence of PhSiH$_3$ as a scavenger. Additional coupling/deprotection cycles using a Fmoc/t-Bu strategy to extend the Lys20 side-chain involved Fmoc-NH-PEG$_2$—CH$_2$COOH (ChemPep Catalog #280102), Fmoc-Glu(OH)-OtBu (ChemPep Catalog #100703) and HOOC—(CH$_2$)$_{16}$—COOtBu. In all couplings, 3 equivalents of the building block are used with PyBOP (3 equiv) and DIEA (6 equiv) in DMF for 4 h at 25° C.

Concomitant cleavage from the resin and side chain protecting group removal are carried out in a solution containing trifluoroacetic acid (TFA): triisopropylsilane:1,2-ethanedithiol:water:thioanisole 90:4:2:2:2 (v/v) for 2 h at 25° C. followed by precipitation with cold ether. Crude peptide is purified to >99% purity (15-20% purified yield) by reversed-phase HPLC chromatography with water/acetonitrile (containing 0.05% v/v TFA) gradient on a C18 column, where suitable fractions are pooled and lyophilized.

In a synthesis performed essentially as described above, the purity of Example 6 is examined by analytical reversed-phase HPLC, and identity is confirmed using LC/MS (ob- The peptide according to Example 7 is synthesized similarly as described above in Example 6. HOOC—(CH$_2$)$_{18}$—COOtBu is incorporated using 3 equivalents of the building block with PyBOP (3 equiv) and DIEA (6 equiv) in DMF for 4h at 25° C. In a synthesis performed essentially as described above in Example 6, the purity of Example 7 is examined by analytical reversed-phase HPLC, and identity is confirmed using LC/MS (observed: $M+3H^+/3=1391.8$; Calculated $M+3H^+/3=1392.6$; observed: $M+4H^+/4=1044.3$; Calculated $M+4H^+/4=1044.7$).

In Vitro Function

Binding Affinity

Binding Affinity of peptides of Examples 1-7 is determined for recombinant human glucagon receptor (hGcg-R), mouse glucagon receptor (mGcg-R) and rat glucagon receptor (rGcg-R). Radioligand competition binding assays using scintillation proximity assay (SPA) methods and membranes prepared from 293HEK stably transfected cells overexpressing hGcg-R, mGcg-R or rGcg-R are run to determine equilibrium dissociation constants ($K_i$) for peptides of Examples 1-7. The experimental protocols and results are described below.

The human Gcg receptor binding assay utilizes cloned hGcg-R (Lok, S, et. al., Gene 140 (2), 203-209 (1994)), isolated from 293HEK cells overexpressing the recombinant hGcg-R. The hGcg-R cDNA is subcloned into the expression plasmid phD (Trans-activated expression of fully gamma-carboxylated recombinant human protein C, an antithrombotic factor. Grinnell, B W, et. al., Bio/Technology 5: 1189-1192 (1987)). This plasmid DNA is transfected into 293HEK cells and selected with 200 µg/mL Hygromycin.

The mouse Gcg receptor binding assay utilizes cloned mouse glucagon receptor (mGcgR) (Burcelin R, Li J, Charron M J. Gene 164 (2), 305-10 (1995) GenBank: L38613) isolated from 293HEK membranes. The mGcgR cDNA is subcloned into the expression plasmid pcDNA3.1 (Promega)-ZeoR. This plasmid DNA is transfected into 293HEK cells and a clonal line selected using 100 µg/mL Zeocin.

The rat Gcg receptor binding assay utilizes cloned rat glucagon receptor (rGcg-R) (Svoboda, M, Ciccarelli, E, Tastenoy, M, Robberecht, P, Christophe, J. A cDNA construct allowing the expression of rat hepatic glucagon receptors. Biochem. Biophys. Res. Commun. 192 (1), 135-142 (1993), GenBank: L04796) in membranes isolated from 293HEK cells transiently expressing rGcg-R. The rGcg-R cDNA is subcloned into the expression plasmid pcDNA3.1 (Promega)-ZeoR. This plasmid DNA is transfected into 293HEK cells and transiently expressed for 48 hours.

Crude plasma membranes are prepared using cells from adherent culture. The cells are lysed on ice in hypotonic buffer containing 50 mM Tris HCl, pH 7.5 and Roche Complete™ Protease Inhibitors with EDTA. The cell suspension is disrupted using a glass Potter-Elvehjem homogenizer fitted with a Teflon® pestle for 25 strokes. The homogenate is centrifuged at 4° C. at 1100×g for 10 minutes. The supernatant is collected and stored on ice while the pellet is resuspended in hypotonic buffer and rehomogenized. The mixture is centrifuged at 1100×g for 10 minutes. The second supernatant is combined with the first supernatant and centrifuged at 35000×g for 1 hour at 4° C. The membrane pellet is resuspended in homogenization buffer containing protease inhibitors, quick frozen in liquid nitrogen and stored as aliquots in a −80° C. freezer until use.

Gcg is radioiodinated by I-125-lactoperoxidase procedure and purified by reverse phase HPLC at Perkin-Elmer (NEX207). The specific activity is 2200 Ci/mmol. $K_D$ determination is performed by homologous competition or saturation binding analysis. The $K_D$ for human Gcg-R is estimated to be 3.92 nM and is used to calculate $K_i$ values for all compounds tested in the hGcg-R assay. The $K_D$ for mouse Gcg-R is estimated to be 3.52 nM and is used to calculate $K_i$ values for all compounds tested in the mGcg-R assay. The $K_D$ for rat Gcg-R is estimated to be 21.4 nM and is used to calculate $K_i$ values for all compounds tested in the rGcg-R assay.

The receptor binding assay is carried out using a Scintillation Proximity Assay (SPA) format with wheat germ agglutinin (WGA) beads (Perkin Elmer). The binding buffer contains 25 mM 4-(2-hydroxyethyl)-1-piperazineethanesulfonic acid (HEPES), pH 7.4, 2.5 mM $CaCl_2$, 1 mM $MgCl_2$, 0.1% (w/v) bacitracin (Affymetrix), 0.003% (w/v) Polyoxyethylenesorbitan monolaurate (TWEEN®-20) and Roche Complete™ Protease Inhibitors without EDTA. Gcg (Eli Lilly and Company) is dissolved in DMSO at 3.48 mg/mL (1 mM) and stored frozen at −20° C. In 100 µL aliquots. The Gcg aliquot is diluted and used in binding assays within an hour. The peptide analogs are dissolved in DMSO and 3-fold serially diluted in 100% DMSO. Next, 5 µL serially diluted compound or DMSO is transferred into Corning® 3632 clear bottom assay plates containing 45 µL at assay binding buffer or unlabeled Gcg control (NSB at 1 µM final). Then, 50 µL at hGcg-R (1.5 µg/well), mGcg-R (6.47 µg/well) or rGcg-R membranes (1.5 µg/well), 50 µL I-125 Gcg (0.15 nM final in reaction), and 50 µL at of WGA beads (150 µg/well) are added, plates sealed and mixed on a plate shaker (setting 6) for 1 minute. Plates are read with a PerkinElmer Trilux MicroBeta® scintillation counter after 12 hours of settling time at room temperature. Results are calculated as a percent of specific I-125-Gcg binding in the presence of compound. The Absolute IC50 concentration of compound is derived by non-linear regression of the percent specific binding of I-125-Gcg vs. the concentration of compound added. The $IC_{50}$ concentration is converted to $K_i$ using the Cheng-Prusoff equation (Cheng, Y., Prusoff, W. H., Biochem. Pharmacol. 22, 3099-3108, (1973)).

$K_i$ of peptides of Examples 1-7 and human Gcg at the hGcg-R, mGcg-R and rGcg-R are provided below in Table 1.

TABLE 1

| | hGcg-R Ki, nM ± SEM, (n) | mGcg-R Ki, nM ± SEM, (n) | rGcg-R Ki, nM ± SEM, (n) |
|---|---|---|---|
| Example 1 | 2.04 ± 1.02 (n = 2) | 1.92 ± 0.71 (n = 2) | 9.78 ± 0.22 (n = 2) |
| Example 2 | 1.07 ± 0.16 (n = 2) | 0.991 ± 0.066 (n = 2) | 5.59 ± 0.24 (n = 2) |
| Example 3 | 0.287 ± 0.171 (n = 2) | 0.174 (n = 1) | 1.56 ± 0.13 (n = 2) |
| Example 4 | 0.738 (n = 1) | 0.774 (n = 1) | 5.86 (n = 1) |
| Example 5 | 1.59 (n = 1) | 1.58 (n = 1) | 4.36 (n = 1) |
| Example 6 | 0.316 (n = 1) | 0.123 (n = 1) | 0.98 (n = 1) |
| Example 7 | 0.673 (n = 1) | 0.753 (n = 1) | 1.38 (n = 1) |
| Human glucagon | 3.64 ± 0.91 (n = 3) | 2.41 ± 0.22 (n = 3) | 23.3 ± 1.7 (n = 3) |

These data indicate that glucagon receptor agonists of the present invention bind to glucagon receptors with affinity similar to or greater than human glucagon in three different species (human, mouse and rat receptors).

Functional Activity and Selectivity

Functional activity and selectivity is determined by quantitation of intracellular cAMP in HEK293 cells expressing human glucagon receptor (hGcg-R), human Glucagon-Like Peptide-1 receptor (hGLP-1R) or human gastric inhibitory peptide (also known as glucose-dependent insulinotropic polypeptide receptor, hGIP-R). The experimental protocols and results are described below.

The hGcg-R functional cAMP assay uses 293HEK cells expressing cloned hGcg-R (Lok, S, et. al., Gene 140 (2), 203-209 (1994)). The hGcg-R cDNA is subcloned into the expression plasmid phD (Trans-activated expression of fully gamma-carboxylated recombinant human protein C, an antithrombotic factor. Grinnell, B W, et. al., Bio/Technology 5: 1189-1192 (1987)). This plasmid DNA is transfected into 293HEK cells and cells are selected with 200 µg/mL Hygromycin.

The hGLP-1-R functional cAMP assay uses 293HEK cells expressing cloned hGLP-1-R (Graziano M P, Hey P J, Borkowski D, Chicchi G G, Strader C D, Biochem Res Commun. 196(1): 141-6, 1993). The hGLP-1R cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5:1189-1192, 1987). This plasmid DNA is transfected into 293HEK cells and cells are selected with 200 µg/mL Hygromycin.

The hGIP-R functional assay uses hGIP-R (Usdin, T. B., Gruber, C., Modi, W. and Bonner, T. I., GenBank: AAA84418.1) cloned into pcDNA3.1 (Promega)-NeoR plasmid. The hGIP-R-pcDNA3.1/Neo plasmid is transfected into Chinese Hamster Ovary cells, CHO-S, for suspension cultures and selected in the presence of 500 µg/mL Geneticin (Invitrogen).

Each receptor over-expressing cell line is treated with peptide in DMEM (Dulbecco's Modified Eagle Medium, Gibco Cat #31053) supplemented with 1× GlutaMAX™ (L-alanyl-L-glutamine dipeptide in 0.85% NaCl, Gibco Cat #35050), 0.1% casein (Sigma Cat #C4765), 250 µM IBMX (3-Isobutyl-1-methylxanthine) and 20 mM HEPES [N-(2-Hydroxyethyl)piperazine-N'-(2-ethanesulfonic acid), HyClone Cat #SH30237.01] in a 40 µµL assay volume. After a 60 minute incubation at room temperature, the resulting increase in intracellular cAMP (adenosine 3',5'-cyclic monophosphate) is quantitatively determined using the CisBio cAMP Dynamic 2 HTRF Assay Kit (CisBio 62AM4PEC). cAMP levels within the cell are detected by adding the cAMP-d2 conjugate in cell lysis buffer (20 µL) followed by the antibody anti-cAMP-Eu$^{3+}$-Cryptate, also in cell lysis buffer (20 µL). The resulting competitive assay is incubated for at least 60 min at room temperature, followed by detection using a PerkinElmer Envision® instrument with excitation at 320 nm and emission at 665 nm and 620 nm. Envision units (emission at 665nm/620nm*10,000) are inversely proportional to the amount of cAMP present and are converted to nM cAMP per well using a cAMP standard curve. The amount of cAMP generated (nM) in each well is converted to a percent of the maximal response observed with either 10 nM human GLP-1(7-36)NH$_2$ (for the hGLP-1R assay), 10 nM human Gcg (for the hGcg-R assay) or 10 nM human GIP(1-42)NH$_2$ (for the hGIP-R assay). A relative $EC_{50}$ value and percent top ($E_{max}$) are derived by non-linear regression analysis using the percent maximal response vs. the concentration of peptide added, fitted to a four-parameter logistic equation.

Functional data for Examples 1-7, human GIP(1-42)NH$_2$, human GLP-1(7-36)NH$_2$ and human Gcg are shown in Table 2 below. Means for $EC_{50}$ are expressed as Geometric means±standard error of the mean (SEM) with the number of replicates (n) indicated in parenthesis. A (>) qualifier indicates that % efficacy did not reach 50% and the calculated $EC_{50}$ is obtained using the highest concentration tested.

TABLE 2

| | hGcg-R $EC_{50}$, nM ± SEM, (n) | hGlp-1R $EC_{50}$, nM ± SEM, (n) | hGIP-R $EC_{50}$, nM ± SEM, (n) |
|---|---|---|---|
| Example 1 | 0.00436 ± 0.00079 (n = 4) | 73.9 ± 19.6 (n = 2) | >500 (n = 3) |
| Example 2 | 0.0112 ± 0.0025 (n = 3) | >100 (n = 2) | >500 (n = 3) |
| Example 3 | 0.00340 ± 0.00010 (n = 2) | >100 (n = 2) | >500 (n = 3) |
| Example 4 | 0.00278 ± 0.00010 (n = 2) | 19.0 ± 8.2 (n = 2) | >500 (n = 3) |
| Example 5 | 0.0160 ± 0.0038 (n = 2) | 27.0 ± 4.5 (n = 2) | >500 (n = 3) |
| Example 6 | 0.00413 ± 0.00026 (n = 2) | >100 (n = 3) | >500 (n = 3) |
| Example 7 | 0.0166 ± 0.0004 (n = 2) | >100 (n = 3) | >500 (n = 3) |
| Human Glucagon | 0.00760 ± 0.00101 (n = 7) | 7.70 ± 1.03 (n = 2) | >500 (n = 3) |
| Human GLP-1 | >10 (n = 1) | 0.076 ± 0.017 (n = 2) | >500 (n = 3) |
| Human GIP | >10 (n = 1) | >10 (n = 1) | 0.145 ± 0.041 (n = 3) |

These data indicate that glucagon receptor agonists of the present invention have similar potency at the glucagon receptor as human glucagon with increased selectivity relative to the GLP-1 receptor and GIP receptor.

Pharmacokinetics

Pharmacokinetics in Rats

Male Sprague Dawley rats are administered a single subcutaneous (100 nmole/kg) dose of an example compound in Tris Buffer (pH 8.0) at a volume of 1 mL/kg. Blood is collected from each animal at 1, 6, 12, 24, 48, 72, 96, 120, 144, 168, 192, and 240 hours postdose.

Plasma concentrations of compounds are determined by LC/MS methods. Each method measured the intact peptide (peptide plus linked time extension). For each assay, the compound and an analog, used as an internal standard (IS), are extracted from 100% rat or monkey plasma (50 µl) using methanol and 0.1% formic acid. Two distinct layers are formed upon centrifugation with the compound and the IS located in the supernatant. A 275 µl aliquot of the supernatant is transferred to a Thermo Protein Precipitation Plate where a vacuum is applied for collection of the flow through into a 96-well plate.

Samples are dried with heated nitrogen gas to remove the supernatant. A volume of 150 µl of 30% acetonitrile and 5% formic acid is added to the wells to reconstitute the samples. Injected samples (20 µl) are loaded onto a Supelco Analytical Discovery BIO Wide Pore C5-3, 5 cm×0.1 mm, 3 µm column. The column effluent is directed into a Thermo Q-Exactive mass spectrometer for detection and quantitation.

Mean Pharmacokinetic Parameters Following a Single 100 nmol/kg Subcutaneous Dose to Male Sprague Dawley Rats are provided in Table 3 below (n=3 for Examples 1, 2 and 5 and Tmax and Cmax for Examples 3 and 4; n=2 for $T_{1/2}$, $AUC_{0\text{-}inf}$ and CL/F for Examples 3 and 4).

TABLE 3

| Compound | $T_{1/2}$ (hr) | Tmax (hr) | Cmax (nmole/L) | $AUC_{0\text{-}inf}$ (hr*nmole/L) | CL/F (mL/hr/kg) |
|---|---|---|---|---|---|
| Example 1 | 13 | 8 | 425 | 11692 | 8.8 |
| Example 2 | 22 | 24 | 346 | 21329 | 4.7 |
| Example 3 | 11 | 8 | 394 | 11133 | 9.2 |
| Example 4 | 16 | 6 | 257 | 5948 | 17.0 |
| Example 5 | 22 | 24 | 237 | 12948 | 7.8 |

Abbreviations: $AUC_{0\text{-}inf}$ = area under the curve from 0 to infinity, CL/F = clearance/bioavailability, Tmax = time to maximum concentration, Cmax = maximum plasma concentration, $T^1/_2$ = half-life, ND = no data.

These data show that Examples 1-5 have an extended duration of action relative to native human glucagon, which has a $T_{1/2}$ of approximately 30 minutes.

Pharmacokinetics in Cynomolgus Monkeys

Male Cynomolgus monkeys are administered a single intravenous (50 nmole/kg) or subcutaneous (50 nmole/kg) dose of a test compound in Tris Buffer (pH 8.0) at a volume of 0.25 ml/kg. Blood is collected from each animal at 0.5 (IV only), 6, 12, 24, 48, 72, 96, 120, 168, 192, 240, 336, 480, 576, and 672 hours post-dose. Plasma concentrations of compounds are determined by LC/MS methods generally as described above in the Sprague dawley rat studies.

Mean (n=2) pharmacokinetic parameters are provided below in table 4.

TABLE 4

| Compound (Route/dose) | Animal_ID | $T_{1/2}$ (hr) | Tmax (hr) | $C_0$ or Cmax (nmole/L) | $AUC_{0-inf}$ (hr*nmole/L) | CL or CL/F (mL/hr/kg) |
|---|---|---|---|---|---|---|
| Example 1 (IV 50 nmol/kg) | Mean | 42 | NA | 1182 | 37278 | 1.36 |
| Example 1 (SC 50 nmol/kg) | Mean | 44 | 9 | 425 | 31821 | 1.57 |
| Example 2 (SC 50 nmol/k) | Mean | 79 | 18 | 377 | 46292 | 1.08 |

Abbreviations: $AUC_{0-inf}$ = area under the curve from 0 to infinity, CL = clearance, CL/F = clearance/bioavailability, Tmax = time to maximal concentration, $C_0$ = concentration extrapolated to time 0 hour, Cmax = maximal plasma concentration, $T^{1/2}$ = half-life, NA = not applicable.

These data show that Examples 1 and 2 have an extended duration of action relative to native human glucagon, which has a $T_{1/2}$ of less than an hour.

In Vivo Studies

Continuous Glucose Monitoring in Rats 12-14 weeks old normal Sprague-Dawley male rats (HARLAN™, Indianapolis, Ind.) are individually housed in a temperature-controlled (24° C.) facility with 12 hour light/dark cycle and free access to food (TD2014 TEKLAD GLOBAL RODENT DIET®, HARLAN™ Labs, Indianapolis, Ind.) and water. After 2 weeks acclimation to the facility, the rats are implanted with HD-XG transmitters (Data Sciences International, St Paul, Minn.).

The transmitter implantation surgery is performed under 2% to 3% isoflurane (2-chloro-2-(difluoromethoxy)-1,1,1-trifluoroethane) anesthesia. The glucose sensor of the transmitter is placed in the descending aorta. The temperature sensor of the transmitter is placed in the abdominal cavity with the transmitter body. Seven days after transmitter implantation surgery, all rats are placed on telemetry receivers to continuously record blood glucose and core body temperature measurements at 1 minute intervals while the rats are moving freely in their home cages. Data acquisition is controlled and analyzed by DATAQUEST A.R.T.™ system software (Data Sciences International, St Paul, Minn.). The initial calibration of the glucose sensor is achieved through an intraperitoneal glucose tolerance test (ipGTT) 7 days post-surgery and subsequent calibrations are made every other day via glucose measurements through tail blood. Beginning on days 9-11 post-surgery, test compounds at 10 nmol/kg dose are administered once by subcutaneous injection in a 20 mM Tris-HCl buffer at pH 8.0, 1 mL/Kg body weight. Blood glucose levels are monitored up to 7 days.

Blood glucose data indicate that Examples 1-7 each result in a sustained increase in blood glucose levels in a dose dependent manner.

Effects on Blood Glucose Concentrations in Dairy Cows

Five non-lactating Holstein dairy cows, averaging 1313 lbs and having completed at least one normal lactation, are treated with escalating doses of Example 6. Cows are initially treated with a subcutaneous injection of 1.5 mg/cow of Example 6. Blood glucose concentrations are measured at various intervals using a hand-held glucometer thru 168 hours post-dosing. For this dosing period and all subsequent dosing periods, blood glucose concentrations measured at time zero serve as the baseline for that period. One week after the initial dose, cows are treated with 5.0 mg/cow SC of Example 6. Blood concentrations are again monitored thru 168 hours following treatment. Finally, two weeks after the 5.0 mg/cow dose of Example 6, all cows are treated with 15 mg/cow SC of Example 6 and blood glucose concentrations are monitored thru 336 hours post-dosing.

Data are provided in Table 5. All doses of Example 6 tested result in an abrupt increase in blood glucose concentrations above baseline concentrations. In addition, the administration of 1.5, 5.0 and 15.0 mg/cow results in sustained increases in blood glucose lasting thru 96, 144 and 312 hours, respectively.

TABLE 5

Blood glucose (mg/dl) in non-lactating dairy cows following subcutaneous injection of Example 6

| Hours Post-dosing | 1.5 mg/cow (n = 5) | 5.0 mg/cow (n = 5) | 15.0 mg/cow (n = 5) |
|---|---|---|---|
| 0 | 61.0 | 57.6 | 59.2 |
| 2 | 70.2** | 75.6** | 88.4** |
| 4 | 76.8** | 76.2** | 71.0* |
| 8 | 74.8** | 75.2** | 65.2 |
| 24 | 66.6^ | 70.4** | 68.2^ |
| 48 | 66.6^ | 75.6** | 74.2** |
| 72 | 72.6** | 72.4** | 78.0** |
| 96 | 68.6** | 68.6* | 76.8** |
| 120 | 64.4 | 67.0* | 70.8* |
| 144 | 58.8 | 67.8* | 72.0* |
| 168 | 57.6 | 63.6 | 73.6** |
| 192 | | | 77.4** |
| 216 | | | 79.2** |
| 240 | | | 75.8** |
| 264 | | | 76.6** |
| 288 | | | 69.4 |
| 312 | | | 71.4* |
| 336 | | | 66.6 |
| SE | 2.3 | 2.8 | 3.8 |

^P < .10,
*P < .05,
**P < .01 vs time 0 (baseline)

Physical and Chemical Characteristics

Solubility and Stability

Samples of Examples 1-6 are prepared at 5 mg/mL in $H_2O$ and dialyzed as described into buffers C6N (10 mM Citrate, 100 mM NaCl, pH 6), C7N (10 mM Citrate, 100 mM NaCl, pH 7), H6.5N (10 mM Histidine, 100 mM NaCl, pH 6.5) and H7.5N (10 mM Histidine, 100 mM NaCl, pH 7.5). Samples are concentrated to 10 mg/mL peptide as described and held at 4° C. for one week. Samples are assessed visually and by SEC-HPLC as described.

Examples 1-6 in all formulations are clear and colorless after one week at 4° C. SEC-HPLC data are provided in Table 6. No significant growth in high molecular weight (HMW) polymer or loss of main peak occurs. Recovery by SEC-HPLC is within 5% for Examples 1-6.

TABLE 6

| | Δ % HMW Peak | | | | |
|---|---|---|---|---|---|
| buffer | Example 1 | Example 2 | Example 3 | Example 4 | Example 6 |
| C6N | 0.13 | −0.03 | −0.01 | 0.64 | −0.03 |
| C7N | 0 | −0.06 | 0.16 | 0.26 | −0.26 |
| H6.5N | −0.02 | 0.06 | −0.03 | 0.35 | 0.11 |
| H7.5N | 0.35 | −0.15 | −0.09 | 0.44 | 0.14 |

| | Δ % Main Peak | | | | |
|---|---|---|---|---|---|
| buffer | Example 1 | Example 2 | Example 3 | Example 4 | Example 6 |
| C6N | −0.02 | 0.08 | 0.08 | −3.42 | −0.98 |
| C7N | 0.26 | −0.26 | −0.18 | −1.19 | 0.36 |
| H6.5N | −0.39 | −1.28 | −0.58 | −2.88 | −1.17 |
| H7.5N | −1.43 | −0.87 | −1.21 | −0.79 | −1.68 |

Solubility of Examples 1-2 is also assessed in three additional formulations: T7 (10 mM Tris-HCl, pH 7), T7Tm (10 mM Tris-HCl, 0.02% polysorbate-20, 29 mM m-cresol, pH 7), and T7Nm (10 mM Tris-HCl, 100 mM NaCl, 29 mM m-cresol, pH 7). Compounds are prepared in T7 via dialysis as described. Samples are formulated at 2 mg/mL in T7, T7Tm or T7Nm then concentrated to 10 mg/mL peptide as described. Formulations are held for one week at 4° C. and assessed visually and by SEC-HPLC and RP-HPLC as described.

All formulations remain clear and colorless. SEC-HPLC and RP-HPLC data are in Table 7. HMW polymer growth does not exceed 0.2% for any formulations. Peak recovery by RP-HPLC is within 5% for all formulations.

TABLE 7

| Peptide | Formulation | % Δ HMW |
|---|---|---|
| Example 1 | T7m | 0.1 |
| | T7Nm | 0.05 |
| | T7Tm | 0.18 |
| Example 2 | T7m | 0.1 |
| | T7Nm | 0.08 |
| | T7Tm | 0.07 |

These data indicates that Examples 1-6 have acceptable solubility properties under different buffer conditions.

Chemical Stability

Chemical stability for Example 1 is determined in different buffers of various pH values. Samples are prepared in $H_2O$ to a 5 mg/mL concentration, dialyzed using Slide-A-Lyzer Dialysis cassettes, 2000 MWCO (part number 66203) overnight at 4° C. into the buffer of interest, filtered through a 0.22 μm filter (Millex, SLGV013SL) then diluted to 1 mg/mL in respective buffer. Buffer compositions are 10 mM Tris-HCl in $H_2O$ pH 8 (T8), 10 mM Tris-HCl in $H_2O$ pH 7 (T7), 10 mM Histidine in $H_2O$ pH 7 (H7), or 10 mM Citrate in $H_2O$ pH 6 (C6). Each 1 mg/mL sample is transferred to three vials. Samples are maintained at 4° C., 25° C. and 40° C. Samples are assessed every two weeks for a total of four weeks. Samples are visually assessed for turbidity and phase separation. Stability of the compound is assessed by analytical reverse phase HPLC (RP-HPLC) on a Waters Symmetry Shield RP18, 3.5 μm, 4.6×100 mm column (part number 18600179) heated at 60° C. with an AB (A=0.1% TFA/$H_2O$, B=0.085% TFA/acetonitrile) gradient of 10% B isocratic over 3 min, 30% B over 3 min, 30-60% B over 30 min, and 95% B over 2 min at a flow rate of 0.9 mL/min (wavelength of 214 nm). Stability is also assessed by size exclusion HPLC (SEC-HPLC) on an Insulin HMWP, 7.8× 300 mm column (part number WAT2015549) with a running buffer of 20 mM Sodium Phosphate, 20% acetonitrile, pH 7.2 running at a flow rate of 0.5 mL/min for 40 min.

Physical appearance is clear to colorless, with no opalescence or particles at pH 7 and pH 8 for Example 1. RP-HPLC and SEC-HPLC results are summarized in Table 8 below. Recovery is within 5% by RP-HPLC and SEC-HPLC which is acceptable.

TABLE 8

| | % Δ main peak by RP at 4 weeks | | | |
|---|---|---|---|---|
| Temp | T8 | T7 | H7 | C6 |
| 4° C. | 3.13% | 2.52% | 1.73% | 2.01% |
| 25° C. | 4.84% | 2.92% | 0.12% | 3.05% |
| 40° C. | 1.41% | 1.74% | 8.69% | 3.61% |

| | % Δ main peak by SEC at 4 weeks | | | |
|---|---|---|---|---|
| Temp | T8 | T7 | H7 | C6 |
| 4° C. | 0.21% | 0.6% | 1.77% | 0.31% |
| 25° C. | 0.17% | 0.1% | 3.1% | 8.72% |
| 40° C. | 0.65% | 0.97% | 1.22% | 1.17% |

Samples in T8 buffer held at 4° C. and 40° C. for four weeks are also analyzed by liquid chromatography-mass spectrometry (LC-MS). No major sites of degradation are identified for Example 1 at pH 8. Overall, chemical stability for Example 1 indicates excellent stability under buffer conditions tested.

Physical Stability

Test samples of Example 1 are prepared via dialysis in T7 buffer then formulated at 2 mg/mL peptide in T7m, T7Nm, and T7Tm as described. Each formulation is transferred to clean glass vials and stirred at 400 rpm via a Teflon-coated magnetic flee at room temperature for 6 hours. Aliquots of 100 μL are taken for assessment at time 0, 1 hour, 3 hours and 6 hours. Samples are assessed visually and by SEC-HPLC as before.

All formulations remain clear and colorless with no opalescence or precipitation. As shown in Table 9, the percentages of peptide in the main peak of SEC-HPLC remains within 5% for all formulations. Data indicate Example 1 has good physical stability characteristics under conditions tested.

TABLE 9

| | % Main Peak | | | |
|---|---|---|---|---|
| Formulation | Time 0 | 1 hour | 3 hours | 6 hours |
| T7m | 95.94 | 96.02 | 96.18 | 95.69 |
| T7Nm | 95.39 | 95.45 | 95.43 | 95.43 |
| T7Tm | 96.21 | 96.12 | 96.27 | 96.18 |

Combination Studies

Activity in Co-Formulation with GIP-GLP-1 Co-Agonist or GLP-1R Agonist

Co-formulations of Examples 1 and 3 with a GIP-GLP-1 co-agonist of SEQ ID NO: 15 or dulaglutide are prepared as described below in the stability studies, and activities of individual compounds and co-formulations are measured using the methods described above. Data are shown in Tables 10 and 11. A (>) qualifier indicates % efficacy did not reach 50% and calculated $EC_{50}$ is obtained using the highest concentration tested.

induced obese (DIO) mice. The GIP-GLP-1 co-agonist has the structure of SEQ ID NO: 14, as described above. The GLP-1R agonist is a GLP-1-Fc fusion described in WO2005000892. Co-formulations are prepared generally as described below in the co-formulation stability studies.

The C57/BL6 DIO animals, although not diabetic, display insulin resistance, dyslipidemia, and hepatic steatosis, all characteristics of metabolic syndrome, after being placed on a high fat (60% Kcal from fat) diet for 12 weeks. Thus, studies in these animals may be used to investigate the effects of proposed therapeutics(s) on parameters such as weight loss, body composition and hepatic steatosis.

TABLE 10

| | | $EC_{50}$ (average of N = 2 ± standard deviation, *N = 1) | | |
|---|---|---|---|---|
| Treatment | Sample Conditions | Gcg Receptor Assay | GLP-1 Receptor Assay | GIP Receptor Assay |
| Example 3 | T7-4 C.-4 wk | 14.3 ± 3.4 pM | >100 nM | >100 nM |
| | T7-40 C.-4 wk | 24.9 ± 2.9 pM | >100 nM | >100 nM |
| | T7m-4 C.-4 wk | 21.1 ± 4.0 pM | >100 nM | >100 nM |
| | T7m-40 C.-4 wk | 21.1 ± 5.1 pM | >100 nM | >100 nM |
| Example 3 + | T7-4 C.-4 wk | 21.3 ± 2.5 pM | 1.47 nM* | 0.65 nM* |
| GIP-GLP-1 | T7-40 C.-4 wk | 21.9 ± 0.4 pM | 2.66 nM* | 0.74 nM* |
| co-agonist | T7m-4 C.-4 wk | 16.0 ± 3.4 pM | 3.08 nM* | 0.71 nM* |
| | T7m-40 C.-4 wk | 24.2 ± 0.5 pM | 2.61 nM* | 0.40 nM* |
| Example 1 | T7-4 C.-4 wk | 20.3 ± 2.5 pM | >100 nM | >100 nM |
| | T7-40 C.-4 wk | 21.7 ± 3.4 pM | 57.53 nM* | >100 nM |
| | T7m-4 C.-4 wk | 23.0 ± 0.3 pM | 43.83 nM* | >100 nM |
| | T7m-40 C.-4 wk | 19.4 ± 5.0 pM | 49.66 nM* | >100 nM |
| Example 1 + | T7-4 C.-4 wk | 23.7 ± 0.7 pM | 1.78 nM* | 0.49 ± 0.16 nM |
| GIP-GLP-1 | T7-40 C.-4 wk | 19.2 ± 2.4 pM | 1.65 nM* | 0.60 ± 0.21 nM |
| co-agonist | T7m-4 C.-4 wk | 16.5 ± 1.8 pM | 1.41 nM* | 0.39 ± 0.06 nM |
| | T7m-40 C.-4 wk | 18.7 ± 0.6 pM | 1.21 nM* | 0.36 ± 0.34 nM |
| GIP-GLP-1 | T7-4 C.-4 wk | >100 nM | 2.56 nM* | 0.70 nM* |
| co-agonist | T7-40 C.-4 wk | >100 nM | 2.76 nM* | 0.41 nM* |
| | T7m-4 C.-4 wk | >100 nM | 1.61 nM* | 0.30 ± 0.19 nM |
| | T7m-40 C.-4 wk | >100 nM | 0.73 nM* | 0.15 ± 0.02 nM |

TABLE 11

| | | $EC_{50}$ (average of N = 2 ± standard deviation | | |
|---|---|---|---|---|
| Peptide | Sample Conditions | Gcg Receptor Assay | GLP-1 Receptor Assay | GIP Receptor Assay |
| Example 1 | C6.5-4 C.-4 wk | 17.8 ± 6.8 pM | 41.6 ± 5.0 nM | >100 nM |
| | C6.5-40 C.-4 wk | 24.3 ± 11.1 pM | 54.6 ± 46.2 nM | >100 nM |
| | C6.5MT-4 C.-4 wk | 18.8 ± 1.8 pM | 55.6 ± 9.2 nM | >100 nM |
| | C6.5MT-40 C.-4 wk | 14.6 ± 5.0 pM | 47.9 ± 5.8 nM | >100 nM |
| Example 3 | C6.5-4 C.-4 wk | 36.9 ± 29.6 pM | >100 nM | >100 nM |
| | C6.5-40 C.-4 wk | 25.7 ± 6.9 pM | >100 nM | >100 nM |
| | C6.5MT-4 C.-4 wk | 19.3 ± 1.1 pM | >100 nM | >100 nM |
| | C6.5MT-40 C.-4 wk | 21.4 ± 3.1 pM | >100 nM | >100 nM |
| Example 1 + | C6.5MT-4 C.-4 wk | 14.6 ± 0.8 pM | 0.36 ± 0.01 nM | >100 nM |
| Dulaglutide | C6.5MT-40 C.-4 wk | 15.2 ± 6.4 pM | 0.37 ± 0.00 nM | >100 nM |
| Example 3 + | C6.5MT-4 C.-4 wk | 22.7 ± 5.2 pM | 0.57 ± 0.25 nM | >100 nM |
| Dulaglutide | C6.5MT-40 C.-4 wk | 22.6 ± 2.1 pM | 0.30 ± 0.01 nM | >100 nM |
| Dulaglutide | C6.5-4 C.-4 wk | 51.9 ± 68.1 nM | 0.37 ± 0.11 nM | >100 nM |
| | C6.5-40 C.-4 wk | >100 nM | 0.31 ± 0.17 nM | >100 nM |
| | C6.5MT-4 C.-4 wk | 54.0 ± 65.0 nM | 0.40 ± 0.14 nM | >100 nM |
| | C6.5MT-40 C.-4 wk | >100 nM | 0.29 ± 0.09 nM | >100 nM |

These data indicate the bioactivity of Examples 1 and 3 is maintained under stressed and non-stressed conditions and/or in combination with a GLP-1R agonist or GIP-GLP-1 co-agonist.

In Vivo Studies of Combinations with GLP-1R Agonists or GIP-GLP-1 Co-Agonists

Effects of combinations of glucagon receptor agonists of the present invention with long-acting GLP-1R agonists or GIP-GLP-1 co-agonists are tested in C57/BL6 dietary 20-21 weeks old male DIO C57/B16 male mice weighing 42-47 g and having initial fat mass ranging from 11.9 g to 17.2 g are used. Animals are individually housed in a temperature-controlled (24° C.) facility with a 12 hour light/dark cycle (lights on 22:00), and have free access to food and water. After 2 weeks acclimation to the facility, mice are randomized to treatment groups (n=5/group) based on body weight so each group has similar starting mean body weight.

Vehicle, test compounds (dose range 3 to 10 nmol/kg), GLP-1R agonist (10 nmol/kg), GIP-GLP-1 co-agonist (10 nmol/kg) or combinations thereof (dose range 3 to 10 nmol/kg) dissolved in vehicle (20 mM Tris-HCl Buffer, pH 8.0) are administered by SC injection to ad libitum fed mice 30-90 minutes prior to onset of the dark cycle every three days for 15 days. SC injections are made on Day 1, 4, 7, 10, and 13. Daily body weight, food intake and glucose are measured throughout the study. Absolute changes in body weight are calculated by subtracting the body weight of the same animal prior to the first injection of molecule. On days 0 and 14, total fat mass is measured by nuclear magnetic resonance (NMR) using an Echo Medical System (Houston, Tex.) instrument.

Daily blood glucose is measured with Accu-Chek glucometer (Roche) from tail vein blood. At the end of the study, animals are sacrificed and livers removed and frozen. Liver triglycerides, determined from homogenates of livers collected at sacrifice, and plasma cholesterol are measured on an Hitachi Modular P clinical analyzer. Statistical comparisons between groups are done using one-way ANOVA followed by Dunnett's multiple comparison test. The $ED_{50}$ values for weight loss lowering are determined in GraphPad Prism using the non-linear fit tool.

Weight loss and percent fat mass change data for studies conducted as described above are provided below in Tables 12 (Example 1) and 13 (Examples 1 and 2). Results in Table 11 are expressed as Mean±SEM of 5 mice per group results in Table 12 are expressed as Mean±SEM of 6 mice per group.

Combinations of Examples 1 and 2 with either GLP-1R agonist or GIP-GLP-1 co-agonist have synergistic effects on body weight and fat mass compared to effects of Examples 1 or 2, GLP-1R agonist or GIP-GLP-1 co-agonist alone (Tables 12 and 13).

TABLE 12

| Treatment | Dose (nmol/kg) | % Change from starting body weight | % Change from starting fat mass |
|---|---|---|---|
| Vehicle | 0 | −3.72 ± 1.169 | −4.39 ± 1.84 |
| Example 1 | 3 | −6.07 ± 1.81 | −9.60 ± 3.35 |
| Example 1 | 10 | −10.56 ± 1.78 | −18.12 ± 3.40* |
| GLP1-R agonist | 10 | −15.54 ± 1.67** | −28.32 ± 2.94*** |
| GLP1-R agonist + Example 1 | 10 + 3 | −26.57 ± 2.05**** | −49.88 ± 3.87**** |
| GLP1-R agonist + Example 1 | 10 + 10 | −30.78 ± 1.97**** | −62.22 ± 4.10**** |
| GIP-GLP-1 co-agonist | 10 | −23.67 ± 1.83**** | −48.21 ± 4.67**** |
| GIP-GLP-1 co-agonist + Example 1 | 10 + 3 | −34.83 ± 3.60**** | −68.99 ± 4.05**** |
| GIP-GLP-1 co-agonist + Example 1 | 10 + 10 | −43.06 ± 2.49**** | −82.06 ± 1.41**** |

*p < 0.05,
**p < 0.01,
***p < 0.001 and
****p < 0.0001 significant from vehicle control group (One-Way ANOVA, Dunnett's).

TABLE 13

| Treatment | Dose (nmol/kg) | % Change from starting body weight | % Change from starting fat mass |
|---|---|---|---|
| Vehicle | 0 | 1.14 ± 1.02 | 3.17 ± 1.61 |
| GLP1-R agonist | 10 | −10.74 ± 1.42* | −21.52 ± 3.51* |
| GIP-GLP-1 co-agonist | 10 | −17.76 ± 4.52*** | −33.30 ± 7.35**** |
| Example 1 | 3 | −1.77 ± 2.08 | −2.08 ± 3.59 |
| Example 1 | 10 | −3.87 ± 1.41 | −6.20 ± 2.90 |
| Example 2 | 3 | −0.85 ± 2.71 | 0.11 ± 5.11 |
| Example 2 | 10 | −5.29 ± 0.84 | −6.03 ± 1.99 |
| GLP1-R agonist + Example 1 | 10 + 3 | −17.49 ± 2.90*** | −34.41 ± 7.38**** |
| GLP1-R agonist + Example 1 | 10 + 10 | −23.49 ± 1.40**** | −48.16 ± 4.14**** |
| GLP1-R agonist + Example 2 | 10 + 3 | −14.83 ± 2.43** | −27.21 ± 6.34** |
| GLP1-R agonist + Example 2 | 10 + 10 | −30.60 ± 4.33**** | −55.55 ± 7.93**** |
| GIP-GLP agonist + Example 1 | 10 + 3 | −18.41 ± 1.23**** | −39.06 ± 4.13**** |
| GIP-GLP agonist + Example 1 | 10 + 10 | −32.01 ± 3.81**** | −65.66 ± 5.92**** |
| GIP-GLP agonist + Example 2 | 10 + 3 | −15.94 ± 1.20*** | −33.54 ± 3.43**** |
| GIP-GLP agonist + Example 2 | 10 + 10 | −40.37 ± 4.03**** | −76.34 ± 3.11**** |

*p < 0.05,
**p < 0.01,
***p < 0.001 and
****p < 0.0001 significant from vehicle control group (One-Way ANOVA, Dunnett's).

Data on effects on blood glucose, plasma cholesterol and liver triglycerides are provided below in tables 14 (mean±SEM, n=5) and 15 (mean±SEM, n=6). Whereas Examples 1 and 2 administered individually increase blood glucose in a dose-dependent manner, combinations of such example glucagon receptor agonists with either GLP-1R agonists or GIP-GLP-1 co-agonists reduce blood glucose, plasma cholesterol and liver triglycerides.

TABLE 14

| Treatment | Dose (nmol/kg) | Blood Glucose AUC (mg/dl/15 day) | Plasma Cholesterol (mg/dl) | Liver Triglycerides (mg/g tissue) |
|---|---|---|---|---|
| Vehicle | 0 | 2224 ± 78.55 | 228.00 ± 6.50 | 200.29 ± 33.67 |
| Example 1 | 3 | 2553 ± 112.5* | 207.00 ± 6.43 | 68.83 ± 5.82**** |
| Example 1 | 10 | 2607 ± 109.4** | 157.80 ± 15.44**** | 32.94 ± 11.23**** |
| GLP1-R agonist | 10 | 1565 ± 26.39**** | 153.40 ± 11.64**** | 55.01 ± 12.62**** |
| GLP1-R agonist + Example 1 | 10 + 3 | 1452 ± 25.48**** | 96.20 ± 7.86**** | 20.89 ± 4.39**** |

TABLE 14-continued

| Treatment | Dose (nmol/kg) | Blood Glucose AUC (mg/dl/15 day) | Plasma Cholesterol (mg/dl) | Liver Triglycerides (mg/g tissue) |
|---|---|---|---|---|
| GLP1-R agonist + Example 1 | 10 + 10 | 1388 ± 80.92**** | 86.60 ± 3.47**** | 12.78 ± 1.57**** |
| GIP-GLP-1 co-agonist | 10 | 1453 ± 27.96**** | 137.80 ± 9.05**** | 32.60 ± 6.70**** |
| GIP-GLP-1 co-agonist + Example 1 | 10 + 3 | 1256 ± 111.5**** | 103.00 ± 3.56**** | 35.47 ± 15.78**** |
| GIP-GLP-1 co-agonist + Example 1 | 10 + 10 | 1044 ± 63.37**** | 77.40 ± 10.10**** | 24.99 ± 13.43**** |

*p < 0.05,
**p < 0.01,
***p < 0.001 from control group (One-Way ANOVA, Dunnett's).

TABLE 15

| Treatment | Dose (nmol/kg) | Blood Glucose AUC (mg/dl/15 day) | Plasma Cholesterol (mg/dl) | Liver Triglycerides (mg/g tissue) |
|---|---|---|---|---|
| Vehicle | 0 | 1806 ± 52.85 | 224.40 ± 5.12 | 174.72 ± 26.56 |
| GLP1-R agonist | 10 | 1189 ± 28.83*** | 149.50 ± 12.02**** | 46.06 ± 12.31**** |
| GIP-GLP-1 co-agonist | 10 | 1137 ± 63.27**** | 135.50 ± 7.11**** | 48.50 ± 7.18**** |
| Example 1 | 3 | 2080 ± 103.2 | 230.50 ± 6.61 | 111.87 ± 22.43** |
| Example 1 | 10 | 2491 ± 110.9**** | 152.83 ± 8.82**** | 29.42 ± 3.54**** |
| Example 2 | 3 | 2433 ± 124.7*** | 201.83 ± 10.11 | 75.45 ± 12.82**** |
| Example 2 | 10 | 2641 ± 186.6**** | 117.67 ± 4.46**** | 16.33 ± 1.53**** |
| GLP1-R agonist + Example 1 | 10 + 3 | 1081 ± 56.68**** | 132.50 ± 19.56**** | 34.34 ± 6.48**** |
| GLP1-R agonist + Example 1 | 10 + 10 | 1031 ± 61.29**** | 83.33 ± 8.50**** | 25.57 ± 7.27**** |
| GLP1-R agonist + Example 2 | 10 + 3 | 1098 ± 52.69**** | 152.00 ± 9.32**** | 38.99 ± 5.96**** |
| GLP1-R agonist + Example 2 | 10 + 10 | 1008 ± 107.2**** | 78.50 ± 6.03**** | 34.42 ± 14.36**** |
| GIP-GLP-1 co-agonist + Example 1 | 10 + 3 | 1142 ± 31.32**** | 131.83 ± 6.42**** | 22.48 ± 3.92**** |
| GIP-GLP-1 co-agonist + Example 1 | 10 + 10 | 916.9 ± 97.73**** | 91.67 ± 4.75**** | 6.99 ± 1.29**** |
| GIP-GLP-1 co-agonist + Example 2 | 10 + 3 | 1063 ± 20.89**** | 119.33 ± 5.79**** | 22.87 ± 5.94**** |
| GIP-GLP-1 co-agonist + Example 2 | 10 + 10 | 801.8 ± 48.21**** | 90.33 ± 7.89**** | 17.99 ± 9.65**** |

*p < 0.05,
**p < 0.01,
***p < 0.001 from control group (One-Way ANOVA, Dunnett's).

Stability in Co-Formulation with GIP-GLP-1 Co-Agonist

Samples of Examples 1 and 3 are prepared and dialyzed against T7 as described. Both examples are formulated separately at 1 mg/mL peptide in T7, T7m, T7N and T7Nm. A GIP-GLP-1 co-agonist of SEQ ID NO: 15 is also prepared and dialyzed against T7 as described for the example glucagon receptor agonists. The GIP-GLP-1 co-agonist is formulated at 1 mg/mL peptide in T7, T7m and T7Nm. Co-formulated samples containing 1 mg/mL Example 1 and 1 mg/mL GIP-GLP-1 co-agonist or 1 mg/mL Example 3 and 1 mg/mL GIP-GLP-1 co-agonist are also prepared and formulated in T7, T7m, T7N and T7Nm. Each formulated sample is transferred to three vials. Samples are maintained at 4° C., 25° C. and 40° C. Samples are assessed every two weeks for a total of four weeks. Samples are visually assessed for turbidity and phase separation. Stability is assessed by RP-HPLC as described above for the single agent formulation. The described RP-HPLC method gives good separation of Example compound and GIP-GLP-1 co-agonist main peaks as well as all degradation peaks produced by stressing the sample at pH 9 and 40° C. for 3 days.

Total peak recovery for all samples is within 5% by RP-HPLC. All formulations remain clear and colorless with no opalescence or precipitation. Changes in the percentage of peptides in their respective main peaks as observed by RP-HPLC after 4 weeks are summarized in Table 16. Loss in percentage of main peak does not significantly change for Example 1 when formulated as a single agent as compared to co-formulations with GIP-GLP-1 co-agonist in all tested formulations. The GIP-GLP-1 co-agonist exhibits consistent loss in the percentage of main peak when formulated as a single agent versus co-formulations with either Example 1 or Example 3. Data indicate that Examples 1 and 3 have acceptable stability when formulated as a single agent or co-formulated with a GIP-GLP-1 co-agonist, and that Examples 1 and 3 do not detrimentally affect GIP-GLP-1 co-agonist stability in co-formulation.

mg/mL of dulaglutide in C6.5 is used to formulate dulaglutide at 3 mg/mL in C6.5 and C6.5MT. Co-formulations in C6.5MT are prepared having 3 mg/mL dulaglutide and 1 mg/mL Example 1, or 3 mg/mL dulaglutide and 1 mg/mL Example 3. Each formulated sample is transferred to three vials and maintained at 4° C., 25° C. and 40° C. Samples are assessed every two weeks for a total of four weeks. Samples are visually assessed for turbidity and phase separation. Stability is assessed by RP-HPLC and SEC-HPLC as described above. Both described HPLC methods give good

TABLE 16

| Compound(s) | Formulation | Change in % Glucagon Analog Main Peak | | | Change in % GIP-GLP-1 co-agonist Main Peak | | |
| --- | --- | --- | --- | --- | --- | --- | --- |
| | | 4° C. | 25° C. | 40° C. | 4° C. | 25° C. | 40° C. |
| Example 1 | T7 | −1.23 | −2.91 | −4.69 | N/A | | |
| | T7m | −0.6 | −0.15 | −2.36 | | | |
| | T7N | −0.29 | −1.39 | −4.19 | | | |
| | T7Nm | −0.38 | −1.71 | −3.93 | | | |
| Example 1 + GIP-GLP-1 co-agonist | T7 | −1.57 | −0.26 | −3.59 | −0.37 | −0.37 | −3.35 |
| | T7m | −1.19 | −0.92 | −2.67 | 0.54 | 0.35 | −3.76 |
| | T7N | −0.25 | −0.89 | −2.15 | −0.21 | −0.57 | −4.42 |
| | T7Nm | −1.22 | −1.94 | −3.78 | −0.71 | −1.07 | −5.50 |
| Example 3 | T7 | −2.23 | −7.00 | −1.78 | N/A | | |
| | T7m | 0.92 | 1.23 | −0.78 | | | |
| | T7N | −1.78 | −6.13 | −2.15 | | | |
| | T7Nm | 0.11 | −0.76 | −2.02 | | | |
| Example 3 + GIP-GLP-1 co-agonist | T7 | −0.07 | −7.51 | −0.80 | −0.40 | −0.40 | −4.14 |
| | T7m | −3.17 | −4.12 | −5.08 | −1.23 | −1.23 | −5.40 |
| | T7N | −3.26 | −7.50 | −6.37 | −0.22 | −1.90 | −6.12 |
| | T7Nm | −2.75 | −3.24 | −3.35 | −0.92 | −0.87 | −4.73 |
| GIP-GLP-1 co-agonist | T7 | N/A | | | −0.59 | −2.12 | −5.25 |
| | T7m | | | | 0.10 | −0.50 | −4.3 |
| | T7Nm | | | | −0.85 | −1.14 | −4.66 |

The samples of Example 1, the GIP-GLP-1 co-agonist and combinations thereof formulated in T7Nm, and combinations of Example 1 and the GIP-GLP-1 co-agonist formulated in T7, which are incubated at 4° C. and 40° C. for four weeks are also assessed by LC-MS. No major sites of degradation are identified. For both Example 1 and GIP-GLP-1 co-agonist, chemical modifications are not significantly different for single agent formulations versus co-formulations.

Stability in Co-Formulation with GLP-1R Agonist

Examples 1 and 3 are prepared and dialyzed against C6.5 (10 mM Citrate pH 6.5) using the same method as described above for preparation into T7 buffer. Compounds are formulated separately at 1 mg/mL peptide in buffer C6.5, C6.5M (10 mM Citrate, 46.4 mg/mL D-mannitol, pH 6.5), C6.5T (10 mM Citrate, 0.02% polysorbate-80, pH 6.5), and C6.5MT (10 mM Citrate, 46.4 mg/mL D-mannitol, 0.02% polysorbate-80, pH 6.5). A stock concentration of 46.5 separation of Example compounds and dulaglutide main peaks as well as all degradation peaks produced by stressing the sample at pH 9 and 40° C. for 3 days.

Total peak recovery for all stability samples is within 5% by both RP-HPLC and SEC-HPLC. All formulations remain clear and colorless with no opalescence or precipitation. Changes in the percentage of compounds in their respective main peaks as observed by SEC-HPLC after four weeks are summarized in Table 17. Examples 1 and 3 are generally stable and do not show a significant loss of main peak. Example 1 does not exhibit less stability when co-formulated with dulaglutide as compared to single agent formulations. Example 3 shows slightly less stability in co-formulation with dulaglutide as compared to single agent formulations. GLP-1R agonist does not exhibit less stability when co-formulated with either Example 1 or 3 as compared to single agent formulations.

TABLE 17

| Compound(s) | Formulation | Glucagon analog Δ % Main Peak | | | GLP-1-Fc Δ % Main Peak | | |
| --- | --- | --- | --- | --- | --- | --- | --- |
| | | 4° C. | 25° C. | 40° C. | 4° C. | 25° C. | 40° C. |
| Example 1 | C6.5 | −1.32 | −1.99 | −2.35 | N/A | | |
| | C6.5M | 0.70 | −1.26 | −1.67 | | | |
| | C6.5T | −2.76 | −3.97 | −1.72 | | | |
| | C6.5MT | −1.04 | −2.65 | −1.40 | | | |
| Example 3 | C6.5 | 1.03 | −0.34 | −0.37 | N/A | | |
| | C6.5M | 0.49 | −0.24 | 1.08 | | | |
| | C6.5T | 0.46 | 0.10 | −0.02 | | | |
| | C6.5MT | 1.02 | −0.07 | 0.64 | | | |

TABLE 17-continued

| Compound(s) | Formulation | Glucagon analog Δ % Main Peak | | | GLP-1-Fc Δ % Main Peak | | |
|---|---|---|---|---|---|---|---|
| | | 4° C. | 25° C. | 40° C. | 4° C. | 25° C. | 40° C. |
| dulaglutide | C6.5 | | N/A | | 0.19 | −0.54 | >−10 |
| | C6.5MT | | | | 0.29 | −0.87 | −0.83 |
| Example 1 + dulaglutide | C6.5MT | −0.67 | −0.75 | −0.75 | 0.25 | −0.16 | −0.16 |
| Example 3 + dulaglutide | C6.5MT | −1.04 | −1.90 | −1.90 | 0.21 | −0.11 | −0.11 |

As observed by RP-HPLC, the stability trends are similar to those observed by SEC-HPLC. Changes in the percentage of compounds in their respective main peaks as observed by RP-HPLC after four weeks are summarized in Table 18. Examples 1 and 3 are generally stable and do not show a significant loss of main peak. Example 1 does not exhibit less stability when co-formulated with the GLP-1R agonist as compared to single agent formulations. Example 3 shows slightly less stability in co-formulation with GLP-1R agonist as compared to single agent formulations. GLP-1R agonist does not exhibit less stability when co-formulated with either Example as compared to single agent formulations.

TABLE 18

| Compound(s) | Formulation | Glucagon Analog Δ % Main Peak | | | GLP-1-Fc Δ % Main Peak | | |
|---|---|---|---|---|---|---|---|
| | | 4° C. | 25° C. | 40° C. | 4° C. | 25° C. | 40° C. |
| Example 1 | C6.5 | −0.06 | −0.47 | −3.73 | | N/A | |
| | C6.5M | 0.34 | −2.61 | −4.47 | | | |
| | C6.5T | 0.51 | −0.35 | −3.57 | | | |
| | C6.5MT | −0.98 | −0.69 | −4.39 | | | |
| Example 3 | C6.5 | 1.06 | 0.17 | 0.24 | | N/A | |
| | C6.5M | 2.43 | 0.64 | 1.86 | | | |
| | C6.5T | −2.11 | * | −3.18 | | | |
| | C6.5MT | −1.22 | * | −0.4 | | | |
| GLP-1R agonist | C6.5 | | N/A | | −1.45 | >−10 | −9.96 |
| | C6.5MT | | | | −0.46 | −0.8 | −7.47 |
| Example 1 + GLP-1R agonist | C6.5MT | 0.62 | * | −2.55 | 1.90 | * | −8.18 |
| Example 3 + GLP-1R agonist | C6.5MT | −0.82 | −2.49 | −1.39 | 0.27 | −3.05 | −9.64 |

* Data not available due to instrument error

Sequences

Human glucagon
SEQ ID NO: 1
HSQGTFTSDYSKYLDSRRAQDFVQWLMNT

Human GLP-1
SEQ ID NO: 2
HAEGTFTSDVSSYLEGQAAKEFIAWLVKGR

Human OXM
SEQ ID NO: 3
HSQGTFTSDYSKYLDSRRAQDFVQWLMNTKRNRNNIA

Human GIP
SEQ ID NO: 4
YAEGTFISDYSIAMDKIHQQDFVNWLLAQKGKKNDWKHNITQ

Glucagon receptor agonist
SEQ ID NO: 5
YX$_1$QGTFX$_2$SDYSKYLDX$_3$KKAX$_4$EFVX$_5$WLLEX$_6$X$_7$ Glucagon receptor agonist
SEQ ID NO: 6
YX$_1$QGTFX$_2$SDYSKYLDX$_3$KKAX$_4$EFVX$_5$WLLEX$_6$X$_7$ wherein
X$_1$ is Aib;
X$_2$ is T or L;
X$_3$ is Aib;
X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H, wherein a is 1 or 2 and b is 14 to 24;
X$_5$ is E or A;
X$_6$ is T or E;
X$_7$ is either absent, or is a peptide selected from the group consisting of GPSSGAPPPS and GPSSG;
and the C-terminal amino acid is optionally amidated.

wherein
X$_1$ is Aib;
X$_2$ is T;
X$_3$ is Aib;
X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H wherein a is 2 and b is 16;
X$_5$ is E;
X$_6$ is T;
X$_7$ is GPSSGAPPPS;
and the C-terminal amino acid is amidated as a C-terminal primary amide.

Glucagon receptor agonist
SEQ ID NO: 7
YX$_1$QGTFX$_2$SDYSKYLDX$_3$KKAX$_4$EFVX$_5$WLLEX$_6$X$_7$ wherein:
$X_1$ is Aib,
$X_2$ is T;
$X_3$ is Aib;
$X_4$ is K which is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H wherein a is 2 and b is 18;
$X_5$ is E;
$X_6$ is T;
$X_7$ is GPSSGAPPPS;
and wherein the C-terminal amino acid is amidated as a C-terminal primaryamide.

Glucagon receptor agonist
SEQ ID NO: 8
YX$_1$QGTFX$_2$SDYSKYLDX$_3$KKAX$_4$EFVX$_5$WLLEX$_6$X$_7$ wherein:
$X_1$ is Aib;
$X_2$ is L;
$X_3$ is Aib;
$X_4$ is K which is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H wherein a is 2 and b is 16;
$X_5$ is E;
$X_6$ is T; and
$X_7$ is GPSSGAPPPS;
and wherein the C-terminal amino acid is amidated as a C-terminal primary amide.

Glucagon receptor agonist
SEQ ID NO: 9
YX$_1$QGTFX$_2$SDYSKYLDX$_3$KKAX$_4$EFVX$_5$WLLEX$_6$X$_7$ wherein $X_I$ is Aib;
$X_2$ is T;
$X_3$ is Aib;
$X_4$ is K which is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H wherein a is 2 and b is 16;
$X_5$ is E;
$X_6$ is T; and
$X_7$ is GPSSG;
and the C-terminal amino acid is amidated as a C-terminal primary amide.

Glucagon receptor agonist
SEQ ID NO: 10
YX$_1$QGTFX$_2$SDYSKYLDX$_3$KKAX$_4$EFVX$_5$WLLEX$_6$X$_7$ wherein $X_I$ is Aib;
$X_2$ is T;
$X_3$ is Aib;
$X_4$ is K which is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H wherein a is 2 and b is 18;
$X_5$ is E;
$X_6$ is T; and
$X_7$ is GPSSG;
and the C-terminal amino acid is amidated as a C-terminal primary amide.

Glucagon receptor agonist
SEQ ID NO: 11
YX$_1$QGTFX$_2$SDYSKYLDX$_3$KKAX$_4$EFVX$_5$WLLEX$_6$X$_7$ wherein
$X_1$ is Aib;
$X_2$ is T;
$X_3$ is Aib;
$X_4$ is K which is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H wherein a is 1 and b is 16;
$X_5$ is A;
$X_6$ is E;
$X_7$ is absent; and
the C-terminal amino acid is C-terminal acid.

Glucagon receptor agonist
SEQ ID NO: 12
YX$_1$QGTFX$_2$SDYSKYLDX$_3$KKAX$_4$EFVX$_5$WLLEX$_6$X$_7$ wherein
$X_1$ is Aib;
$X_2$ is T;
$X_3$ is Aib;
$X_4$ is K which is chemically modified through conjugation to the epsilon-amino group of the K side-chain with ([2-(2-Amino-ethoxy)-ethoxy]-acetyl)$_2$-($\gamma$Glu)$_a$-CO—(CH$_2$)$_b$—CO$_2$H wherein a is 1 and b is 18;
$X_5$ is A;
$X_6$ is E;
$X_7$ is absent; and
the C-terminal amino acid is C-terminal acid.

GIP-GLP co-agonist
SEQ ID NO: 13
YX$_1$EGTFTSDYSIX$_2$LDKIAQX$_3$AX$_4$VQWLIAGGPSSGAPPPS;

wherein
$X_1$ is Aib;
$X_2$ is Aib;
$X_3$ is K which is chemically modified through conjugation to the epsilon-amino group of the K side-chain with ([2-(2-amino-ethoxy)-ethoxy]-acetyl)$_2$-($\gamma$Glu)$_b$—CO$_2$H wherein a is 1 or 2 and b is 10 to 20;
$X_4$ is Phe or 1-naphthylalanine (1-Nal);
and the C-terminal amino acid is optionally amidated.

GIP-GLP co-agonist
SEQ ID NO: 14
YX$_1$EGTFTSDYSIX$_2$LDKIAQX$_3$AX$_4$VQWLIAGGPSSGAPPPS;

wherein
$X_1$ is Aib;
$X_2$ is Aib;
$X_3$ is K which is chemically modified through conjugation to the epsilon-amino group of the K side-chain with ([2-(2-amino-ethoxy)-ethoxy]-acetyl)$_2$-($\gamma$Glu)$_a$-CO(CH$_2$)$_b$—CO$_2$H wherein a is 2 and b is 18;
$X_4$ is 1-Nal;
and the C-terminal amino acid is amidated as a C-terminal primary amide.

GIP-GLP co-agonist

SEQ ID NO: 15

YX$_1$EGTFTSDYSIX$_2$LDKIAQX$_3$AX$_4$VQWLIAGGPSSGAPPPS;

wherein
X$_1$ is Aib;
X$_2$ is Aib;
X$_3$ is K which is chemically modified through conjugation to the epsilon-amino group of the K side-chain with ([2-(2-amino-ethoxy)-ethoxy]-acetyl)$_2$-(γGlu)$_a$-CO(CH$_2$)$_b$—CO$_2$H wherein a is 1 and b is 18;
X$_4$ is Phe;
and the C-terminal amino acid is amidated as a C-terminal primary amide.

Glucagon receptor agonist

SEQ ID NO: 16

YX$_1$QGTFX$_2$SDYSKYLDX$_3$KKAX$_4$EFVX$_5$WLLEX$_6$X$_7$ wherein
X$_1$ is Aib;
X$_2$ is T or L;
X$_3$ is Aib;
X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H, wherein a is 2 and b is 14 to 24;
X$_5$ is E;
X$_6$ is T;
X$_7$ is a peptide selected from the group consisting of GPSSGAPPPS and GPSSG;
and the C-terminal amino acid is amidated.

Glucagon receptor agonist

SEQ ID NO: 17

YX$_1$QGTFX$_2$SDYSKYLDX$_3$KKAX$_4$EFVX$_5$WLLEX$_6$X$_7$ wherein
X$_1$ is Aib;
X$_2$ is T;
X$_3$ is Aib;
X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H,
wherein a is 1 and b is 14 to 24;
X$_5$ is A;
X$_6$ is E; and
X$_7$ is absent.

We claim:

1. A glucagon receptor agonist compound comprising the formula:

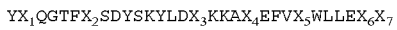
YX$_1$QGTFX$_2$SDYSKYLDX$_3$KKAX$_4$EFVX$_5$WLLEX$_6$X$_7$ wherein
X$_1$ is Aib;
X$_2$ is T;
X$_3$ is Aib;
X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H, wherein a is 1 and b is 18;
X$_5$ is A;
X$_6$ is E; and
X$_7$ is absent;
(SEQ ID NO: 12);
or a pharmaceutically acceptable salt thereof.

2. A glucagon receptor agonist compound consisting of the formula:

YX$_1$QGTFX$_2$SDYSKYLDX$_3$KKAX$_4$EFVX$_5$WLLEX$_6$X$_7$ wherein
X$_1$ is Aib;
X$_2$ is T;
X$_3$ is Aib;
X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H, wherein a is 1 and b is 18;
X$_5$ is A;
X$_6$ is E; and
X$_7$ is absent;
(SEQ ID NO: 12);
or a pharmaceutically acceptable salt thereof.

3. A glucagon receptor agonist compound comprising the formula:

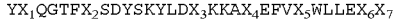
YX$_1$QGTFX$_2$SDYSKYLDX$_3$KKAX$_4$EFVX$_5$WLLEX$_6$X$_7$ wherein
X$_1$ is Aib;
X$_2$ is T;
X$_3$ is Aib;
X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H, wherein a is 1 and b is 16;
X$_5$ is A;
X$_6$ is E; and
X$_7$ is absent;
(SEQ ID NO: 11);
or a pharmaceutically acceptable salt thereof.

4. A glucagon receptor agonist compound consisting of the formula:

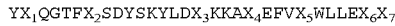
YX$_1$QGTFX$_2$SDYSKYLDX$_3$KKAX$_4$EFVX$_5$WLLEX$_6$X$_7$ wherein
X$_1$ is Aib;
X$_2$ is T;
X$_3$ is Aib;
X$_4$ is K which is chemically modified through conjugation to the epsilon-amino group of the K side-chain with ([2-(2-Amino-ethoxy)-ethoxy]-acetyl)$_2$-(γGlu)$_a$-CO—(CH$_2$)$_b$—CO$_2$H, wherein a is 1 and b is 16;
X$_5$ is A;
X$_6$ is E; and
X$_7$ is absent;
(SEQ ID NO: 11);
or a pharmaceutically acceptable salt thereof.

5. A method of treating fatty liver comprising administering to a bovine in need thereof, an effective amount of the glucagon receptor agonist of claim 1.

6. The method of claim 5 wherein the bovine is a dairy cow.

7. A pharmaceutical composition comprising the glucagon receptor agonist of claim 1 and a pharmaceutically acceptable carrier, diluent, or excipient.

8. The glucagon receptor agonist of claim 1, wherein the activity of the glucagon receptor agonist at the glucagon receptor is at least 100-fold higher than the potency of the glucagon receptor agonist at the GLP-1 receptor.

9. A method of treating fatty liver comprising administering to a bovine in need thereof, an effective amount of the glucagon receptor agonist claim 3.

10. The method of claim 9 wherein the bovine is a dairy cow.

11. A pharmaceutical composition comprising the glucagon receptor agonist of claim 3 and a pharmaceutically acceptable carrier, diluent, or excipient.

12. The glucagon receptor agonist of claim 3, wherein the activity of the glucagon receptor agonist at the glucagon receptor is at least 100-fold higher than the potency of the glucagon receptor agonist at the GLP-1 receptor.

* * * * *

SEQUENCE LISTING

```
<160> NUMBER OF SEQ ID NOS: 17

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 30
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 37
<212> TYPE: PRT
<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35
```

```
<210> SEQ ID NO 4
<211> LENGTH: 42
<212> TYPE: PRT
<213> ORGANISM: Homo sapiens

<400> SEQUENCE: 4

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 5
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (7)..(7)
<223> OTHER INFORMATION: Xaa at pos. 7 is Thr or Leu
<220> FEATURE:
<221> NAME/KEY: MISC_FEATURE
<222> LOCATION: (16)..(16)
<223> OTHER INFORMATION: Xaa at pos. 16 is alpha Aminoisobutyric acid
<220> FEATURE:
<221> NAME/KEY: MOD_RES
<222> LOCATION: (20)..(20)
<223> OTHER INFORMATION: Xaa at pos. 20 is Lys which is chemically
      modified through conjugation to the epsilon-amino group of the
      Lys side-chain with ([2-(2-Amino-ethoxy)-ethoxy]-acetyl)2-(gamma-
      Glu)a-CO-(CH2)b-CO2H, wherein a is 1 or 2 and b is 14 to 24
<220> FEATURE:
<221> NAME/KEY: MISC_FEATURE
<222> LOCATION: (24)..(24)
<223> OTHER INFORMATION: Xaa at pos. 24 is Glu or Ala.
<220> FEATURE:
<221> NAME/KEY: MISC_FEATURE
<222> LOCATION: (29)..(29)
<223> OTHER INFORMATION: Xaa at pos. 29 is Thr or Glu.
<220> FEATURE:
<221> NAME/KEY: MISC_FEATURE
<222> LOCATION: (30)..(30)
<223> OTHER INFORMATION: Xaa at pos. 30 is either: absent, or a
      polypeptide selected from the group consisting of GPSSGAPPPS and
      GPSSG, and the C-terminal amino acid is optionally amidated

<400> SEQUENCE: 5

Tyr Xaa Gln Gly Thr Phe Xaa Ser Asp Tyr Ser Lys Tyr Leu Asp Xaa
1               5                   10                  15

Lys Lys Ala Xaa Glu Phe Val Xaa Trp Leu Leu Glu Xaa Xaa
            20                  25                  30

<210> SEQ ID NO 6
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
```

```
<222> LOCATION: (16)..(16)
<223> OTHER INFORMATION: Xaa at pos. 16 is alpha Aminoisobutyric acid
<220> FEATURE:
<221> NAME/KEY: MOD_RES
<222> LOCATION: (20)..(20)
<223> OTHER INFORMATION: Xaa at pos. 20 is Lys which is chemically
      modified through conjugation to the epsilon-amino group of the Lys
      side-chain with ([2-(2-Amino-ethoxy)-ethoxy]-acetyl)2-(gamma-
      Glu)a-CO-(CH2)b-CO2H wherein a is 2 and b is 16.
<220> FEATURE:
<221> NAME/KEY: MOD_RES
<222> LOCATION: (39)..(39)
<223> OTHER INFORMATION: Ser at pos. 39 is amidated as a C-terminal
      primary amide

<400> SEQUENCE: 6

Tyr Xaa Gln Gly Thr Phe Thr Ser Asp Tyr Ser Lys Tyr Leu Asp Xaa
1               5                   10                  15

Lys Lys Ala Xaa Glu Phe Val Glu Trp Leu Leu Glu Thr Gly Pro Ser
            20                  25                  30

Ser Gly Ala Pro Pro Pro Ser
        35

<210> SEQ ID NO 7
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (16)..(16)
<223> OTHER INFORMATION: Xaa at pos. 16 is alpha Aminoisobutyric acid
<220> FEATURE:
<221> NAME/KEY: MOD_RES
<222> LOCATION: (20)..(20)
<223> OTHER INFORMATION: Xaa at pos. 20 is Lys which is chemically
      modified through conjugation to the epsilon-amino group of the Lys
      side-chain with ([2-(2-Amino-ethoxy)-ethoxy]-acetyl)2-(gamma-
      Glu)a-CO-(CH2)b-CO2H wherein a is 2 and b is 18
<220> FEATURE:
<221> NAME/KEY: MOD_RES
<222> LOCATION: (39)..(39)
<223> OTHER INFORMATION: Ser at pos. 39 is amidated as a C-terminal
      primary amide

<400> SEQUENCE: 7

Tyr Xaa Gln Gly Thr Phe Thr Ser Asp Tyr Ser Lys Tyr Leu Asp Xaa
1               5                   10                  15

Lys Lys Ala Xaa Glu Phe Val Glu Trp Leu Leu Glu Thr Gly Pro Ser
            20                  25                  30

Ser Gly Ala Pro Pro Pro Ser
        35

<210> SEQ ID NO 8
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (16)..(16)
```

```
<223> OTHER INFORMATION: Xaa at pos. 16 is alpha Aminoisobutyric acid
<220> FEATURE:
<221> NAME/KEY: MOD_RES
<222> LOCATION: (20)..(20)
<223> OTHER INFORMATION: Xaa at pos. 20 is Lys which is chemically
      modified through conjugation to the epsilon-amino group of the Lys
      side-chain with ([2-(2-Amino-ethoxy)-ethoxy]-acetyl)2-(gamma-
      Glu)a-CO-(CH2)b-CO2H wherein a is 2 and b is 16
<220> FEATURE:
<221> NAME/KEY: MOD_RES
<222> LOCATION: (39)..(39)
<223> OTHER INFORMATION: Ser at pos. 39 is amidated as a C-terminal
      primary amide

<400> SEQUENCE: 8

Tyr Xaa Gln Gly Thr Phe Leu Ser Asp Tyr Ser Lys Tyr Leu Asp Xaa
1               5                   10                  15

Lys Lys Ala Xaa Glu Phe Val Glu Trp Leu Leu Glu Thr Gly Pro Ser
            20                  25                  30

Ser Gly Ala Pro Pro Pro Ser
        35

<210> SEQ ID NO 9
<211> LENGTH: 34
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (16)..(16)
<223> OTHER INFORMATION: Xaa at pos. 16 is alpha Aminoisobutyric acid
<220> FEATURE:
<221> NAME/KEY: MISC_FEATURE
<222> LOCATION: (20)..(20)
<223> OTHER INFORMATION: Xaa at pos. 20 is Lys which is chemically
      modified through conjugation to the epsilon-amino group of the Lys
      side-chain with ([2-(2-Amino-ethoxy)-ethoxy]-acetyl)2-(gamma-
      Glu)a-CO-(CH2)b-CO2H wherein a is 2 and b is 16
<220> FEATURE:
<221> NAME/KEY: MOD_RES
<222> LOCATION: (34)..(34)
<223> OTHER INFORMATION: The Gly at pos. 34 is amidated as a C-terminal
      primary amide

<400> SEQUENCE: 9

Tyr Xaa Gln Gly Thr Phe Thr Ser Asp Tyr Ser Lys Tyr Leu Asp Xaa
1               5                   10                  15

Lys Lys Ala Xaa Glu Phe Val Glu Trp Leu Leu Glu Thr Gly Pro Ser
            20                  25                  30

Ser Gly

<210> SEQ ID NO 10
<211> LENGTH: 34
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (16)..(16)
<223> OTHER INFORMATION: Xaa at pos. 16 is alpha Aminoisobutyric acid
<220> FEATURE:
```

```
<221> NAME/KEY: MISC_FEATURE
<222> LOCATION: (20)..(20)
<223> OTHER INFORMATION: Xaa at pos. 20 is Lys which is chemically
      modified through conjugation to the epsilon-amino group of the Lys
      side-chain with ([2-(2-Amino-ethoxy)-ethoxy]-acetyl)2-(gamma-
      Glu)a-CO-(CH2)b-CO2H wherein a is 2 and b is 18
<220> FEATURE:
<221> NAME/KEY: MOD_RES
<222> LOCATION: (34)..(34)
<223> OTHER INFORMATION: Gly at pos. 34 is amidated as a C-terminal
      primary amide

<400> SEQUENCE: 10

Tyr Xaa Gln Gly Thr Phe Thr Ser Asp Tyr Ser Lys Tyr Leu Asp Xaa
1               5                   10                  15

Lys Lys Ala Xaa Glu Phe Val Glu Trp Leu Leu Glu Thr Gly Pro Ser
            20                  25                  30

Ser Gly

<210> SEQ ID NO 11
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (16)..(16)
<223> OTHER INFORMATION: Xaa at pos. 16 is alpha Aminoisobutyric acid
<220> FEATURE:
<221> NAME/KEY: MISC_FEATURE
<222> LOCATION: (20)..(20)
<223> OTHER INFORMATION: Xaa at pos. 20 is Lys which is chemically
      modified through conjugation to the epsilon-amino group of the Lys
      side-chain with ([2-(2-Amino-ethoxy)-ethoxy]-acetyl)2-(gamma-
      Glu)a-CO-(CH2)b-CO2H wherein a is 1 and b is 16
<220> FEATURE:
<221> NAME/KEY: MOD_RES
<222> LOCATION: (29)..(29)
<223> OTHER INFORMATION: Glu at pos. 29 is C-terminal acid

<400> SEQUENCE: 11

Tyr Xaa Gln Gly Thr Phe Thr Ser Asp Tyr Ser Lys Tyr Leu Asp Xaa
1               5                   10                  15

Lys Lys Ala Xaa Glu Phe Val Ala Trp Leu Leu Glu Glu
            20                  25

<210> SEQ ID NO 12
<211> LENGTH: 29
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (16)..(16)
<223> OTHER INFORMATION: Xaa at pos. 16 is alpha Aminoisobutyric acid
<220> FEATURE:
<221> NAME/KEY: MISC_FEATURE
<222> LOCATION: (20)..(20)
<223> OTHER INFORMATION: Xaa at pos. 20 is Lys which is chemically
      modified through conjugation to the epsilon-amino group of the Lys
      side-chain with ([2-(2-Amino-ethoxy)-ethoxy]-acetyl)2-(gamma-
      Glu)a-CO-(CH2)b-CO2H wherein a is 1 and b is 18
```

```
<220> FEATURE:
<221> NAME/KEY: MOD_RES
<222> LOCATION: (29)..(29)
<223> OTHER INFORMATION: Glu at pos. 29 is C-terminal acid.

<400> SEQUENCE: 12

Tyr Xaa Gln Gly Thr Phe Thr Ser Asp Tyr Ser Lys Tyr Leu Asp Xaa
1               5                   10                  15

Lys Lys Ala Xaa Glu Phe Val Ala Trp Leu Leu Glu Glu
            20                  25

<210> SEQ ID NO 13
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (13)..(13)
<223> OTHER INFORMATION: Xaa at pos. 13 is alpha Aminoisobutyric acid
<220> FEATURE:
<221> NAME/KEY: MISC_FEATURE
<222> LOCATION: (20)..(20)
<223> OTHER INFORMATION: Xaa at pos. 20 is Lys which is chemically
      modified through conjugation to the epsilon-amino group of the Lys
      side-chain with ([2-(2-amino-ethoxy)-ethoxy]-acetyl)2-(gamma-
      Glu)a-CO(CH2)b-CO2H wherein a is 1 or 2 and b is 10 to 20
<220> FEATURE:
<221> NAME/KEY: MISC_FEATURE
<222> LOCATION: (22)..(22)
<223> OTHER INFORMATION: Xaa at pos. 22 is Phe or 1-naphthylalanine
      (1-Nal)
<220> FEATURE:
<221> NAME/KEY: MOD_RES
<222> LOCATION: (39)..(39)
<223> OTHER INFORMATION: Ser at pos. 39 is optionally amidated

<400> SEQUENCE: 13

Tyr Xaa Glu Gly Thr Phe Thr Ser Asp Tyr Ser Ile Xaa Leu Asp Lys
1               5                   10                  15

Ile Ala Gln Xaa Ala Xaa Val Gln Trp Leu Ile Ala Gly Gly Pro Ser
            20                  25                  30

Ser Gly Ala Pro Pro Ser
        35

<210> SEQ ID NO 14
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (13)..(13)
<223> OTHER INFORMATION: Xaa at pos. 13 is alpha Aminoisobutyric acid
<220> FEATURE:
<221> NAME/KEY: MISC_FEATURE
<222> LOCATION: (20)..(20)
<223> OTHER INFORMATION: Xaa at pos. 20 is Lys which is chemically
      modified through conjugation to the epsilon-amino group of the Lys
      side-chain with ([2-(2-amino-ethoxy)-ethoxy]-acetyl)2-(gamma-
      Glu)a-CO(CH2)b-CO2H wherein a is 2 and b is 18
<220> FEATURE:
```

<221> NAME/KEY: MISC_FEATURE
<222> LOCATION: (22)..(22)
<223> OTHER INFORMATION: Xaa at pos. 22 is 1-Nal
<220> FEATURE:
<221> NAME/KEY: MOD_RES
<222> LOCATION: (39)..(39)
<223> OTHER INFORMATION: Ser at pos. 39 is amidated as a C-terminal
      primary amide

<400> SEQUENCE: 14

Tyr Xaa Glu Gly Thr Phe Thr Ser Asp Tyr Ser Ile Xaa Leu Asp Lys
1               5                   10                  15

Ile Ala Gln Xaa Ala Xaa Val Gln Trp Leu Ile Ala Gly Gly Pro Ser
            20              25                  30

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (13)..(13)
<223> OTHER INFORMATION: Xaa at pos. 13 is alpha Aminoisobutyric acid
<220> FEATURE:
<221> NAME/KEY: MISC_FEATURE
<222> LOCATION: (20)..(20)
<223> OTHER INFORMATION: Xaa at pos. 20 is Lys which is chemically
      modified through conjugation to the epsilon-amino group of the Lys
      side-chain with ([2-(2-amino-ethoxy)-ethoxy]-acetyl)2-(gamma-
      Glu)a-CO(CH2)b-CO2H wherein a is 1 and b is 18
<220> FEATURE:
<221> NAME/KEY: MOD_RES
<222> LOCATION: (39)..(39)
<223> OTHER INFORMATION: Ser at pos. 29 is amidated as a C-terminal
      primary amide

<400> SEQUENCE: 15

Tyr Xaa Glu Gly Thr Phe Thr Ser Asp Tyr Ser Ile Xaa Leu Asp Lys
1               5                   10                  15

Ile Ala Gln Xaa Ala Phe Val Gln Trp Leu Ile Ala Gly Gly Pro Ser
            20              25                  30

Ser Gly Ala Pro Pro Pro Ser
        35

<210> SEQ ID NO 16
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (7)..(7)
<223> OTHER INFORMATION: Xaa at pos. 7 is Thr or Leu
<220> FEATURE:
<221> NAME/KEY: MISC_FEATURE
<222> LOCATION: (16)..(16)
<223> OTHER INFORMATION: Xaa at pos. 16 is alpha Aminoisobutyric acid
<220> FEATURE:

```
<221> NAME/KEY: MOD_RES
<222> LOCATION: (20)..(20)
<223> OTHER INFORMATION: Xaa as pos. 20 is Lys which is chemically
      modified through conjugation to the epsilon-amino group of the Lys
      side-chain with ([2-(2-Amino-ethoxy)-ethoxy]-acetyl)2-
      (gamma Glu)a-CO-(CH2)b-CO2H, wherein a is 2 and b is 14 to 24
<220> FEATURE:
<221> NAME/KEY: MISC_FEATURE
<222> LOCATION: (24)..(24)
<223> OTHER INFORMATION: Xaa as pos. 24 is Glu
<220> FEATURE:
<221> NAME/KEY: MISC_FEATURE
<222> LOCATION: (29)..(29)
<223> OTHER INFORMATION: Xaa as pos. 29 is Thr
<220> FEATURE:
<221> NAME/KEY: MISC_FEATURE
<222> LOCATION: (30)..(30)
<223> OTHER INFORMATION: Xaa as pos. 30 is a peptide selected from the
      group consisting of GPSSGAPPPS and GPSSG;and the C-terminal amino
      acid is amidated

<400> SEQUENCE: 16

Tyr Xaa Gln Gly Thr Phe Xaa Ser Asp Tyr Ser Lys Tyr Leu Asp Xaa
1               5                   10                  15

Lys Lys Ala Xaa Glu Phe Val Xaa Trp Leu Leu Glu Xaa Xaa
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at pos. 2 is alpha Aminoisobutyric acid
<220> FEATURE:
<221> NAME/KEY: MISC_FEATURE
<222> LOCATION: (7)..(7)
<223> OTHER INFORMATION: Xaa at pos. 7 is Thr
<220> FEATURE:
<221> NAME/KEY: MISC_FEATURE
<222> LOCATION: (16)..(16)
<223> OTHER INFORMATION: Xaa at pos. 16 is alpha Aminoisobutyric acid
<220> FEATURE:
<221> NAME/KEY: MOD_RES
<222> LOCATION: (20)..(20)
<223> OTHER INFORMATION: Xaa as pos. 20 is Lys which is chemically
      modified through conjugation to the epsilon-amino group of the K
      side-chain with ([2-(2-Amino-ethoxy)-ethoxy]-acetyl)2-(gamma
      Glu)a-CO-(CH2)b-CO2H, wherein a is 1 and b is 14 to 24
<220> FEATURE:
<221> NAME/KEY: MISC_FEATURE
<222> LOCATION: (24)..(24)
<223> OTHER INFORMATION: Xaa at pos. 24 is Ala
<220> FEATURE:
<221> NAME/KEY: MISC_FEATURE
<222> LOCATION: (29)..(29)
<223> OTHER INFORMATION: Xaa at pos. 29 is Glu
<220> FEATURE:
<221> NAME/KEY: MISC_FEATURE
<222> LOCATION: (30)..(30)
<223> OTHER INFORMATION: Xaa at pos. 30 is absent

<400> SEQUENCE: 17

Tyr Xaa Gln Gly Thr Phe Xaa Ser Asp Tyr Ser Lys Tyr Leu Asp Xaa
1               5                   10                  15

Lys Lys Ala Xaa Glu Phe Val Xaa Trp Leu Leu Glu Xaa Xaa
            20                  25                  30
```